(12) United States Patent
Patolsky et al.

(10) Patent No.: US 10,667,750 B2
(45) Date of Patent: Jun. 2, 2020

(54) METHOD AND SYSTEM FOR SENSING BY MODIFIED NANOSTRUCTURE

(71) Applicant: Ramot at Tel-Aviv University Ltd., Tel-Aviv (IL)

(72) Inventors: Fernando Patolsky, Rehovot (IL); Vadim Krivitsky, Bney-Ayish (IL); Marina Zverzhinetsky, Rishon-LeZion (IL)

(73) Assignee: Ramot at Tel-Aviv University Ltd., Tel-Aviv (IL)

( * ) Notice: Subject to any disclaimer, the term of this patent is extended or adjusted under 35 U.S.C. 154(b) by 0 days.

(21) Appl. No.: 16/060,423

(22) PCT Filed: Dec. 8, 2016

(86) PCT No.: PCT/IL2016/051319
§ 371 (c)(1),
(2) Date: Jun. 8, 2018

(87) PCT Pub. No.: WO2017/098517
PCT Pub. Date: Jun. 15, 2017

(65) Prior Publication Data
US 2018/0372678 A1 Dec. 27, 2018

Related U.S. Application Data

(60) Provisional application No. 62/264,944, filed on Dec. 9, 2015, provisional application No. 62/264,913, filed on Dec. 9, 2015.

(51) Int. Cl.
*A61B 5/00* (2006.01)
*G01N 33/50* (2006.01)
(Continued)

(52) U.S. Cl.
CPC .......... *A61B 5/4866* (2013.01); *A61B 5/1473* (2013.01); *A61B 5/6833* (2013.01);
(Continued)

(58) Field of Classification Search
CPC ... H01L 23/532; H01L 29/06; H01L 29/0673; H01L 29/16; A61B 5/4866; A61B 5/1473
See application file for complete search history.

(56) References Cited

U.S. PATENT DOCUMENTS 3,935,071 A    1/1976   Bergmeyer et al.
7,619,290 B2   11/2009  Lieber et al.
(Continued)

FOREIGN PATENT DOCUMENTS

EP    1669748    6/2006
EP    1806414    7/2007
(Continued)

OTHER PUBLICATIONS

Notice of Reasons for Rejection dated Oct. 9, 2018 From the Japan Patent Office Re. Application No. 2016-525073 and Its Translation Into English. (10 Pages).
(Continued)

*Primary Examiner* — Matthew L Reames

(57) ABSTRACT

A method of detecting a presence and/or concentration of a marker, e.g., a marker, in a liquid, e.g., a liquid, is disclosed. The method comprises: contacting the liquid with a sensor having an immobilized affinity moiety interacting with the marker and being configured to generate a detectable signal responsively to the interaction. The method further comprises washing the liquid off the sensor, and detecting the presence and/or concentration of the marker based on a detectable signal received from the sensor within a time-window beginning a predetermined time period after a beginning time of the washing.

16 Claims, 29 Drawing Sheets
(24 of 29 Drawing Sheet(s) Filed in Color)

(51) Int. Cl.
  G01N 27/414    (2006.01)
  H01L 23/532    (2006.01)
  H01L 29/06     (2006.01)
  A61B 5/1473    (2006.01)
  H01L 29/16     (2006.01)
  B82Y 15/00     (2011.01)
  H01L 51/00     (2006.01)
  H01L 51/05     (2006.01)

(52) U.S. Cl.
  CPC ....... *A61B 5/6847* (2013.01); *G01N 27/4146* (2013.01); *G01N 33/5005* (2013.01); *H01L 23/532* (2013.01); *H01L 29/06* (2013.01); *H01L 29/0673* (2013.01); *H01L 29/16* (2013.01); *B82Y 15/00* (2013.01); *H01L 51/0049* (2013.01); *H01L 51/0545* (2013.01); *H01L 51/0558* (2013.01)

(56) References Cited

U.S. PATENT DOCUMENTS

| | | |
|---|---|---|
| 7,632,234 B2 | 12/2009 | Manda et al. |
| 10,274,456 B2 | 4/2019 | Patolsky et al. |
| 2009/0124025 A1 | 5/2009 | Hamilton et al. |
| 2010/0022012 A1 | 1/2010 | Lieber et al. |
| 2010/0093019 A1 | 4/2010 | Ditcham et al. |
| 2010/0140110 A1 | 6/2010 | Kim et al. |
| 2010/0256344 A1 | 10/2010 | Thompson et al. |
| 2010/0325073 A1 | 12/2010 | Haick |
| 2011/0233059 A1 | 9/2011 | Grundig et al. |
| 2016/0258899 A1 | 9/2016 | Patolsky et al. |
| 2019/0200923 A1 | 7/2019 | Patolsky et al. |
| 2019/0234900 A1 | 8/2019 | Patolsky et al. |

FOREIGN PATENT DOCUMENTS

| | | |
|---|---|---|
| JP | 2009-540798 | 11/2009 |
| JP | 2010-515887 | 5/2010 |
| JP | 2012-511156 | 5/2012 |
| WO | WO 2004/034025 | 4/2004 |
| WO | WO 2005/004204 | 1/2005 |
| WO | WO 2008/027078 | 3/2008 |
| WO | WO 2008/030395 | 3/2008 |
| WO | WO 2008/083446 | 7/2008 |
| WO | WO 2009/104180 | 8/2009 |
| WO | WO 2010/115143 | 10/2010 |
| WO | WO 2011/000443 | 1/2011 |
| WO | WO 2012/082494 | 6/2012 |
| WO | WO 2012/137207 | 10/2012 |
| WO | WO 2015/059704 | 4/2015 |
| WO | WO 2017/098517 | 6/2017 |
| WO | WO 2017/098518 | 6/2017 |

OTHER PUBLICATIONS

Communication Pursuant to Article 94(3) EPC dated May 9, 2017 From the European Patent Office Re. Application No. 14796555.2. (6 Pages).
Communication Pursuant to Article 94(3) EPC dated Feb. 20, 2018 From the European Patent Office Re. Application No. 14796555.2. (6 Pages).
International Preliminary Report on Patentability dated May 6, 2016 From the International Bureau of WIPO Re. Application No. PCT/IL2014/050921.
International Search Report and the Written Opinion dated Feb. 23, 2015 From the International Searching Authority Re. Application No. PCT/IL2014/050921.
International Search Report and the Written Opinion dated Mar. 26, 2017 From the International Searching Authority Re. Application No. PCT/IL2016/051319. (12 Pages).
International Search Report and the Written Opinion dated Mar. 29, 2017 From the International Searching Authority Re. Application No. PCT/IL2016/051320. (12 Pages).
Notice of Eligibility for Grant and Examination Report dated Jun. 11, 2018 From the Intellectual Property Office of Sinagpore, IPOS Re. Application No. 11201602976X. (7 Pages).
Official Action dated Jul. 5, 2018 From the US Patent and Trademark Office Re. U.S. Appl. No. 15/030,886. (54 pages).
Search Report and Written Opinion dated Sep. 21, 2016 From the Intellectual Property Office of Singapore Re. Application No. 11201602976X.
Written Opinion dated Sep. 6, 2017 From the Intellectual Property Office of Singapore, IPOS Re. Application No. 11201602976X. (8 Pages).
Chen et al. "Label-Free Cytokine Micro- and Nano-Biosensing Towards Personalized Medicine of Systemic Inflammatory Disorders", Advanced Drug Delivery Reviews, 95: 90-103, Available Online Sep. 15, 2015. p .4, r-h Col., 1st Para, Fig.3.
Chen et al. "Silicon Nanowire Filed-Effect Transistor-Based Biosensors for Biomedical Diagnosis and Cellular Recording Investigation", Nano Today, 6(2): 131-154, Available Online Mar. 8, 2011.
Clavaguera et al. "Sup-PPM Detection of Nerve Agents Using Chemically Functionalized Silicon Nanoribbon Field-Effect Transistors", Angewandte Chemie International Edition, 49(24): 4063-4066, Jun. 2010.
Cui et al. "Nanowire Nanosensors for Highly Sensitive and Selective Detection of Biological and Chemical Species", Science, 293(5533): 1289-1292, Aug. 17, 2001.
De et al. "Integrated Label-Free Silicon Naonowire Sensor Arrays for (Bio)Chemical Analysis", The Analyst, XP055168035, 138(11): 3221-3229, Jan. 2013. Fig.2, figs.1-3, Abstract, p. 4, 2nd Col.
Duan et al. "Intracellular Recordings of Action Potentials by an Extracellular Nanoscale Field-Effect Transistor", Nature Nanotechnology, 7(3): 174-179, Published Online Dec. 18, 2011.
Garcia et al. "Enhanced Determination of Glucose by Microchip Electrophoresis With Pulsed Amperometric Detection", Analytica Chimica Acta, 508(1): 1-9, Apr. 15, 2004.
Garcia-Perez et al. "Metabolic Fingerprinting With Capillary Electrophoresis", Journal of Chromatography A, 1204(2): 130-139, Available Online Jul. 12, 2008.
Griffin et al. "Metabolic Profiles of Cancer Cells", Nature Reviews Cancer, 4(7): 551-561, Jul. 2004.
Holcomb et al. "Electrode Array Detector for Microchip Capillary Electrophoresis", The Analyst, 134(3): 486-492, Published Online Dec. 3, 2008.
Hsiung et al. "Multiplex Reatl-Time Monitoring of Cellular Metabolic Activity Using a Redox-Reactive Nanowire Biosensor", 17th International Conference on Miniaturized Systems for Chemistry and Life Sciences, Freiburg, Germany, Oct. 27-31, 2013, XP055167304, p. 1959-1961, Oct. 2013.
Huang et al. "Real-Time and Label-Free Detection of the Prostate-Specific Antigen in Human Serum by A Polycrystalline Silicon Nanowire Field-Effect Transistor Biosensor", Analytical Chemistry, 85(16): 7912-7918, Jul. 11, 2013. p. 7914, r-h Col., 1st Para, Figs.3b, 4b, 6.
Jeykumari et al. "Covalent Modification of Multiwalled Carbon Nanotubes with Neutral Red for the Fabrication of an Amperometric Hydrogen Peroxide Sensor", Nanotechnology 18(125501): 1-10, 2007.
Kleps et al. "Investigation of Silver-, Meso- and Nanoporous Silicon Composite Layers for Biomedical Applications", Romanian Journal of Information Science and Technology, 10(1): 97-111, 2007.
Kosaka et al. "Detection of Cancer Biomarkers in Serum Using a Hybrid Mechanical and Optoplasmonic Nanosensor", Nature Nanotechnology, 9(12): 1047-1053, Published Online Nov. 2, 2014.
Kraly et al. "Review: Microfluidic Applications in Metabolomics and Metabolic Profiling", Analytica Chimica Acta, 653(1): 23-35, Available Online Sep. 1, 2009.
Krivitsky et al. "Antigen-Dissociation From Antibody-Modified Nanotransistor Sensor Arrays as a Direct Biomarker Detection Method in Unprocessed Biosamples", Nano Letters, 16(10): 6272-6281, Aug. 31, 2016.

(56) References Cited

OTHER PUBLICATIONS

Krivitsky et al. "Si Nanowires Forest-Based On-Chip Biomolecular Filtering, Separation and Preconcentration Devices: Nanowires Do It All", Nano Letters, 12(9): 4748-4756, Aug. 2, 2012.
Li et al. "Sequence-Specific Label-Free DNA Sensors Based on Silicon Nanowires", Nano Letters, 4(2): 245-247, Published on Web Jan. 8, 2004.
Lin et al. "Microscale LC-MS-NMR Platform Applied to the Identification of Active Cyanobacterial Metabolites", Analytical Chemistry, 80(21): 8045-8054, Nov. 1, 2008.
Lu et al. "A Nano-Ni Based Ultrasensitive Nonenzymatic Electrochemical Sensor for Glucose: Enhancing Sensitivity Through a Nanowire Array Strategy", Biosensors and Bioelectronics, 25(1): 218-223, Published Online Jul. 7, 2009.
Lu et al. "Enzyme-Functionalized Gold Nanowires for the Fabrication of Biosensors", Bioelectrochemistry, 71(2): 211-216, Published Online Jun. 14, 2007.
Lu et al. "Label-Free and Rapid Electrical Detection of hTSH With CMOS-Compatible Silicon Nanowire Transistor Arrays", ACS Applied Materials & Interfaces, 6(22): 20378-20384, Oct. 22, 2014. Figs.4a, 4b, Table 1, p. 20381, 1-h Col., Last Para.
Marx "Tracking Metastasis and Tricking Cancer", Nature, 494(7435): 131-136, Feb. 7, 2013.
McAlpine et al. "Highly Ordered Nanowire Arrays on Plastic Substrates for Ultrasensitive Flexible Chemical Sensors", Nature Materials, 6(5): 379-384, May 2007.
Mohanty et al. "Field Effect Transistor Nanosensor for Breast Cancer Diagnostics", ArXiv Preprint ArXiv, 1401.1168: 1-25, Jan. 6, 2014. p. 5, Section B, p. 10, 2nd Para, p. 14, 3rd Para.
Mu et al. "Silicon Nanowire Field-Effect Transistors—A Versatile Class of Potentiometric Nanobiosensors", IEEE Access, 3: 287-302, Apr. 22, 2015. p. 293, 1-h Col., 4th Para, p. 290, r-h Col., 1st Para.
Munoz-Pinedo et al. "Cancer Metabolism: Current Perspectives and Future Directions", Cell Death and Disease, 3(1): e248-1-e248-10, Published Online Jan. 12, 2012.
Noor et al. "Silicon Nanowires as Field-Effect Transducers for Biosensor Development: A Review", Analytica Chimica Acta, 825: 1-25, Available Online May 15, 2014.
Northen et al. "Clathrate Nanostructures for Mass Spectrometry", Nature, 449(7165): 1033-1037, Oct. 25, 2007.
Patolsky "Nanotechnology Tools in Biology and Medicine Applications", YouTube [Online], Presentation, Summer School on Nanomedicine and Innovation, The Marian Gertner Institute for Medical Nanosystems, Raymond and Beverly Sackler School of Chemistry, Tel Aviv University, Israel, Jun. 19, 2014. Video: 45:13-49:10 (mm:ss).
Patolsky et al. "Electrical Detection of Single Viruses", Proc. Natl. Acad. Sci. USA, PNAS, 101(39): 14017-14022, Sep. 28, 2004.
Patolsky et al. "Fabrication of Silicon Nanowire Devices for Ultrasensitive, Label- Free, Real-Time Detection of Biological and Chemical Species", Nature Protocols, 1(4): 1711-1724, Published Online Nov. 16, 2006.
Patolsky et al. "Nanowire-Based Biosensors", Analytical Chemistry, 78(13): 4260-4269, Jul. 1, 2006.
Peretz-Soroka et al. "Optically-Gated Self-Calibrating Nanosensors: Monitoring pH and Metabolic Activity of Living Cells", Nano Letters, 13(7): 3157-3168, Jun. 17, 2013.
Ramgir et al. "Nanowire-Based Sensors", Small, 6(16): 1705-1722, Aug. 17, 2010.
Shaijumon et al. "Catalytic Growth of Carbon Nanotubes Over Ni/Cr Hydrotalcite-Type Anionic Clay and Their Hydrogen Storage Properties", Applied Surface Science, 242: 192-198, 2005.
Shao et al. "Silicon Nanowire Sensors for Bioanalytical Applications: Glucose and Hydrogen Peroxide Detection", Advanced Functional Materials, 15(9): 1478-1482, Sep. 2005.
Shulaev "Metabolomics Technology and Bioinformatics", Briefings in Bioinformatics, 7(2): 128-139, May 18, 2006.
Stern et al. "Label-Free Biomarker Detection From Whole Blood", Nature Nanotechnology, 5(2): 138-142, Published Online Dec. 13, 2009.
Stern et al. "Semiconducting Nanowire Field-Effect Transistor Biomolecular Sensors", IEEE Transactions on Electron Devices, 55(11): 3119-3130, Nov. 2008.
Su et al. "A Silicon Nanowire-Based Electrochemical Sensor With High Sensitivity and Electrocatalytic Activity", Particle Particle Systems Characterization, 30(4): 326-331, Apr. 2013.
Telg et al. "G- and G+ in the Raman Spectrum of Isolated Nanotube: A Study on Resonance Conditions and Lineshape", Physica Status Solidi (b), 245(10): 2189-2192, 2008.
Timko et al. "Electrical Recording From Hearts With Flexible Nanowire Device Arrays", Nano Letters, 9(2): 914-918, Published on Web Jan. 26, 2009.
Tyagi et al. "Patternable Nanowire Sensors for Electrochemical Recording of Dopamine", Analytical Chemistry, 81(24): 9979-9984, Dec. 15, 2009.
Vlckova et al. "Determination of Cationic Neutrotransmitters and Metabolites in Brain Homogenates by Microchip Electrophoresis and Carbon Nanotube-Modified Amperometry", Journal of Chromatography A, 1142(2): 214-221, 2007.
Wanekeya et al. "Nanowire-Based Electrochemical Biosensors", Electroanalysis, XP055167317, 18(6): 533-550, Mar. 1, 2006.
Wang et al. "A NEMS Thermal Biosensor for Metabolic Monitoring Applications", Journal of Microelectromechanical Systems, 17(2): 318-327, Apr. 2008.
Wang et al. "Simultaneous Microchip Enzymatic Measurements of Blood Lactate and Glucose", Analytica Chimica Acta, 585(1): 11-16, Published Online Dec. 9, 2006.
Yang et al. "Gold Nanoparticle Modified Silicon Nanowires as Biosensors", Nanotechnology, 17(11): S276-S279, May 19, 2006.
Yin et al. "A Hydrogen Peroxide Electrocheinical Sensor Based on Silver Nanopartides Decorated Silicon Nanowire Arrays" Electrochimica Acta, 56: 3884-3889, 2011.
Yun et al. "On-Line Carbon Nanotube-Based Biosensors in Microfluidic Channels", Nanosensors, Microsensors, and Biosensors and Systems, Proceedings of the SPIE, XP055167836, 6528: 65280-1-65280-10, Apr. 4, 2007. Abstract, Figs.3-5.
Zayats et al. "An Integrated NAD+-Dependent Enzyme-Functionalized Field-Effect Transistor (ENFET) System: Development of a Lactate Biosensor", Biosensor & Bioelectronics, XP055450950, 15(11-12): 671-680, Dec. 1, 2000.
Zheng et al. "Multiplexed Electrical Detection of Cancer Markers With Nanowire Sensor Arrays", Nature Biotechnology, 23(10): 1294-1301, Oct. 2005.
Supplementary European Search Report and the Euorpan Search Opinion dated Jul. 11, 2019 From the European Patent Office Re. Application No. 16872559.6. (10 Pages).
Supplementary European Search Report and the European Search Opinion dated Jul. 10, 2019 From the European Patent Office Re. Application No. 16872558.8. (12 Pages).
Elnathan et al. "Biorecognition Layer Engineering: Overcoming Screening Limitations of Nanowire-Based FET Devices", Nano Letters, XP055366864, 12(10): 5245-5254, Published Online Sep. 10, 2012.
Gao et al. "General Strategy for Biodetection in High Ionic Strength Solutions Using Transistor-Based Nanoelectronic Sensors", Nano Letters, XP055317106, 15(3): 2143-2148, Published Online Feb. 9, 2015.
Hwang et al. "Biodegradable Elastomers and Silicon Nanomembranes/Nanoribbons for Stretchable, Transient Electronics, and Biosensors", Nano Letters, XP055601726, 15(5): 2801-2808, Published Online Feb. 23, 2015.
Kim et al. "Direct Label-Free Electrical Immunodetection in Human Serum Using a Flow-Through-Apparatus Approach With Integrated Field-Effect Transistors", Biosensors and Bioelectronics, XP029490340, 25(7): 1767-1773, Available Online Dec. 29, 2009.
Rajan et al. "Performance Limitations for Nanowire/Nanoribbon Biosensors", Wiley Interdisciplinary Reviews: Nanomedicine and Nanobiotechnology, XP055593106, 5(6): 629-645, Published Online Jul. 29, 2013.
Ramachandran et al. "A Rapid, Multiplexed, High-Throughput Flow-Through Membrane Immunoassay: A Convenient Alternative to ELISA", Diagnostics, XP055549823, 3(2): 244-260, Published Online Apr. 2, 2013.
Official Action dated Mar. 27, 2020 from the US Patent and Trademark Office Re. U.S. Appl. No. 16/297,665. (41 pages).

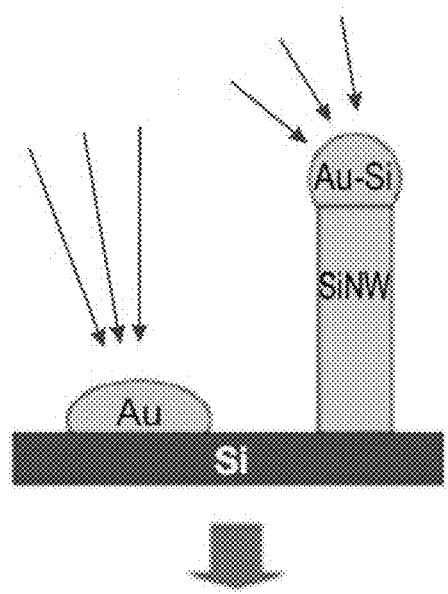
FIG. 1C
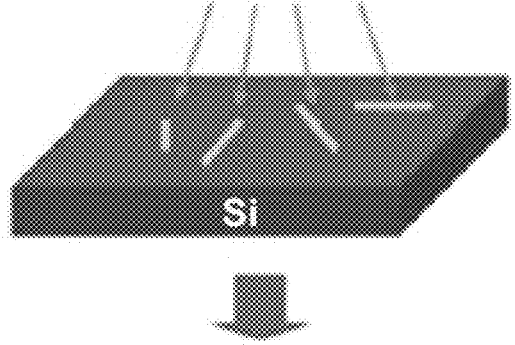
FIG. 1D
FIG. 1E
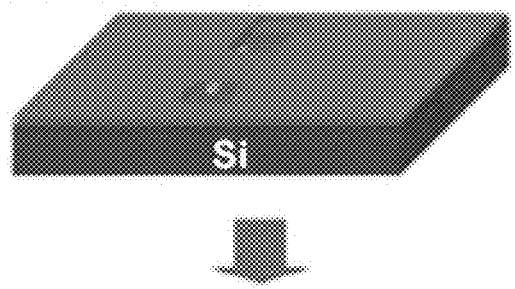
FIG. 1F
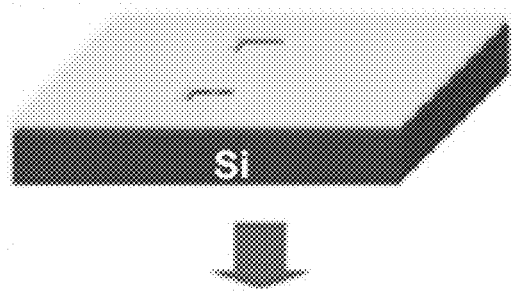
FIG. 1G
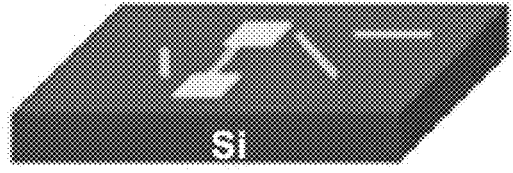

METHOD AND SYSTEM FOR SENSING BY MODIFIED NANOSTRUCTURE

RELATED APPLICATIONS

This application is a National Phase of PCT Patent Application No. PCT/IL2016/051319 having International filing date of Dec. 8, 2016, which claims the benefit of priority under 35 USC § 119(e) of U.S. Provisional Patent Applications Nos. 62/264,913 and 62/264,944, both filed on Dec. 9, 2015. The contents of the above applications are all incorporated by reference as if fully set forth herein in their entirety.

FIELD AND BACKGROUND OF THE INVENTION

The present invention, in some embodiments thereof, relates to sensing and, more particularly, but not exclusively, to a methods and system for detecting a marker, such as, but not limited to, a biomarker, in a liquid, such as, but not limited to, biological liquid.

The development of efficient bio-molecular separation and purification techniques is of high importance in modern genomics, proteomics, and bio-sensing areas, primarily due to the fact that most bio-samples are mixtures of high diversity and complexity. Most of the currently-practiced techniques lack the capability to rapidly and selectively separate and concentrate specific target proteins from a complex bio-sample, and are difficult to integrate with lab-on-a-chip sensing devices.

Semiconducting nanowires are known to be extremely sensitive to chemical species adsorbed on their surfaces. For a nanowire device, the binding of a charged analyte the surface of the nanowire leads to a conductance change, or a change in current flowing through the wires. The 1D (one dimensional) nanoscale morphology and the extremely high surface-to-volume ratio make this conductance change to be much greater for nanowire-based sensors versus planar FETs (field-effect transistors), increasing the sensitivity to a point that single molecule detection is possible.

Nanowire-based field-effect transistors (NW-FETs) have therefore been recognized in the past decade as powerful potential new sensors for the detection of chemical and biological species. See, for example, Patolsky et al., Analytical Chemistry 78, 4260-4269 (2006); Stern et al., IEEE Transactions on Electron Devices 55, 3119-3130 (2008); Cui et al., Science 293, 1289-1292 (2001); Patolsky et al. Proceedings of the National Academy of Sciences of the United States of America 101, 14017-14022 (2004), all being incorporated by reference as if fully set forth herein.

Studies have also been conducted with nanowire electrical devices for the simultaneous multiplexed detection of multiple biomolecular species of medical diagnostic relevance, such as DNA and proteins [Zheng et al., Nature Biotechnology 23, 1294-1301 (2005); Timko et al., Nano Lett. 9, 914-918 (2009); Li et al., Nano Lett. 4, 245-247 (2004)].

Generally, in a NW-FET configuration, the gate potential controls the channel conductance for a given source drain voltage (VSD), and modulation of the gate voltage (VGD) changes the measured source-drain current (ISD). For NW sensors operated as FETs, the sensing mechanism is the field-gating effect of charged molecules on the carrier conduction inside the NW. Compared to devices made of micro-sized materials or bulk materials, the enhanced sensitivity of nanodevices is closely related to the reduced dimensions and larger surface/volume ratio. Since most of the biological analyte molecules have intrinsic charges, binding on the nanowire surface can serve as a molecular gate on the semiconducting SiNW [Cui et al., 2001, supra].

Antibody/enzyme nanowire FET devices which target metabolites via binding affinity have been disclosed in, for example, Lu et al. *Bioelectrochemistry* 2007, 71(2): 211-216; Patolsky et al. Nanowire-based biosensors. *Anal Chem* 2006, 78(13): 4260-4269; and Yang et al. *Nanotechnology* 2006, 17(11): S276-S279.

Electrochemically-sensitive nanowire sensors for detecting metabolites by oxidative reactions have been disclosed in, for example, Lu et al. Biosens Bioelectron 2009, 25(1): 218-223; Shao et al. Adv Funct Mater 2005, 15(9): 1478-1482; Su et al. Part Part Syst Char 2013, 30(4): 326-331; and Tyagi et al. *Anal Chem* 2009, 81(24): 9979-9984.

U.S. Pat. No. 7,619,290, U.S. Patent Application having publication No. 2010/0022012, and corresponding applications, teach nanoscale devices composed of, inter alia, functionalized nanowires, which can be used as sensors.

Clavaguera et al. disclosed a method for sub-ppm detection of nerve agents using chemically functionalized silicon nanoribbon field-effect transistors [Clavaguera et al., Angew. Chem. Int. Ed. 2010, 49, 1-5].

$SiO_2$ surface chemistries were used to construct a 'nanoelectronic nose' library, which can distinguish acetone and hexane vapors via distributed responses [Nature Materials Vol. 6, 2007, pp. 379-384].

U.S. Patent Application having Publication No. 2010/0325073 discloses nanodevices designed for absorbing gaseous NO. WO 2011/000443 describes nanodevices which utilize functionalized nanowires for detecting nitro-containing compounds.

Duan et al. [Nature Nanotechnology, Vol. 7, 2012, pp. 174-179] describes a silicon nanowire FET detector and an electrically insulating SiO2 nanotube that connects the FET to the intracellular fluid (the cytosol). When there is a change in transmembrane potential Vm, the varying potential of the cytosol inside the nanotube gives rise to a change in the conductance G of the FET.

Kosaka et al. [Nature Nanotechnology, Vol. 9, 2014, pp. 1047-1053] discloses detection of cancer biomarkers in serum using surface-anchored antibody.

Krivitsky et al. [Nano letters 2012, 12(9): 4748-4756] describe an on-chip all-SiNW filtering, selective separation, desalting, and preconcentration platform for the direct analysis of whole blood and other complex biosamples. The separation of required protein analytes from raw biosamples is first performed using a antibody-modified roughness-controlled SiNWs forest of ultralarge binding surface area, followed by the release of target proteins in a controlled liquid media, and their subsequent detection by SiNW-based FETs arrays fabricated on the same chip platform.

WO 2015/059704 discloses an integrated microfluidic nanostructure sensing system, comprised of one or more sensing compartments featuring a redox-reactive nanostructure FET array which is in fluid communication with one or more sample chambers. This system has been shown to perform multiplex real-time monitoring of cellular metabolic activity in physiological solutions, and was demonstrated as an efficient tool in promoting the understanding of metabolic networks and requirements of cancers for personalized medicine.

Additional background art includes, for example, Chen et al., Nano Today (2011) 6, 131-54, and references cited therein; and Stern et al., Nature Nanotechnology, 2009.

SUMMARY OF THE INVENTION

According to an aspect of some embodiments of the present invention there is provided a method of detecting a presence and/or concentration of a marker in a liquid. The method comprises: contacting the liquid with a sensor having an immobilized affinity moiety interacting with the marker and being configured to generate a detectable signal responsively to the interaction. The method also comprises washing the liquid off the sensor; and detecting the presence and/or concentration of the marker based on a detectable signal received from the sensor within a time-window beginning a predetermined time period after a beginning time of the washing.

According to some embodiments of the invention the marker is a biomarker.

According to some embodiments of the invention the liquid is a biological liquid.

According to some embodiments of the invention the detection is not based on signal received from the sensor before the beginning time of the time-window.

According to some embodiments of the invention the predetermined time period is at least 30 seconds.

According to some embodiments of the invention the method comprises monitoring the detectable signal from the beginning of the washing, and identifying the beginning of the time-window based on a change in a time-dependence of the signal.

According to some embodiments of the invention the affinity moiety comprises an immunogenic moiety.

According to some embodiments of the invention the immunogenic moiety comprises an antibody or a fragment thereof.

According to some embodiments of the invention the immunogenic moiety comprises an antigen and wherein the marker is a biomarker which comprises an antibody to the antigen.

According to some embodiments of the invention the affinity moiety comprises a ligand and the marker is a biomarker which comprises a receptor.

According to some embodiments of the invention the method comprises contacting the liquid with a sensor which is non-specific to the marker and washing the liquid also off the non-specific sensor, wherein the detection of the presence and/or concentration of the marker is based on a comparison between the detectable signal and a background signal received from the non-specific sensor.

According to an aspect of some embodiments of the present invention there is provided a system for detecting a presence and/or concentration of a marker in a liquid. The system comprises a fluidic device having a sensing chamber and a sensor in the sensing chamber, the sensor having an immobilized affinity moiety interacting with the marker and being configured to generate a detectable signal responsively to the interaction; a flow control system for introducing a washing buffer to the chamber to wash the liquid off the sensor; and a signal analyzer for analyzing detectable signal received from the sensor over a time-window beginning a predetermined time period after a beginning time of the washing, to detect the presence and/or concentration of the marker.

In any of the embodiments, the interaction is optionally and preferably characterized by a $K_D$ which is equal or less than $10^{-5}$ M or a $K_D$ which is equal or less than $10^{-6}$ M or a $K_D$ which is equal or less than $10^{-7}$ M or a $K_D$ which is equal or less than $10^{-8}$ M or a $K_D$ which is equal or less than $10^{-9}$ M or a $K_D$ which is equal or less than $10^{-10}$ M.

According to some embodiments of the invention the signal analyzer is configured to discard from the analysis signal received from the sensor before the beginning time of the time-window.

According to some embodiments of the invention the signal analyzer is configured for monitoring the detectable signal from the beginning of the washing, and identifying the beginning of the time-window based on a change in a time-dependence of the signal.

According to some embodiments of the invention the beginning of the time-window is defined at a time point at which a rate of change of the signal, in absolute value, is below a predetermined threshold.

According to some embodiments of the invention the fluidic device further comprises a sensor that is non-specific the marker in the sensing chamber, signal analyzer is configured for comparing between the detectable signal and a background signal received from the non-specific sensor, to detect the presence and/or concentration of the marker based on the comparison.

According to some embodiments of the invention the sensor is a nanostructure and the affinity moiety is immobilized on a surface of the nanostructure.

According to some embodiments of the invention the sensor is a transistor.

According to some embodiments of the invention the sensor is a transistor, having a nanostructure as a channel and wherein the affinity moiety is immobilized on a surface of the nanostructure.

According to some embodiments of the invention the transistor is a field-effect transistor.

BRIEF DESCRIPTION OF SEVERAL VIEWS OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

Figure 2:
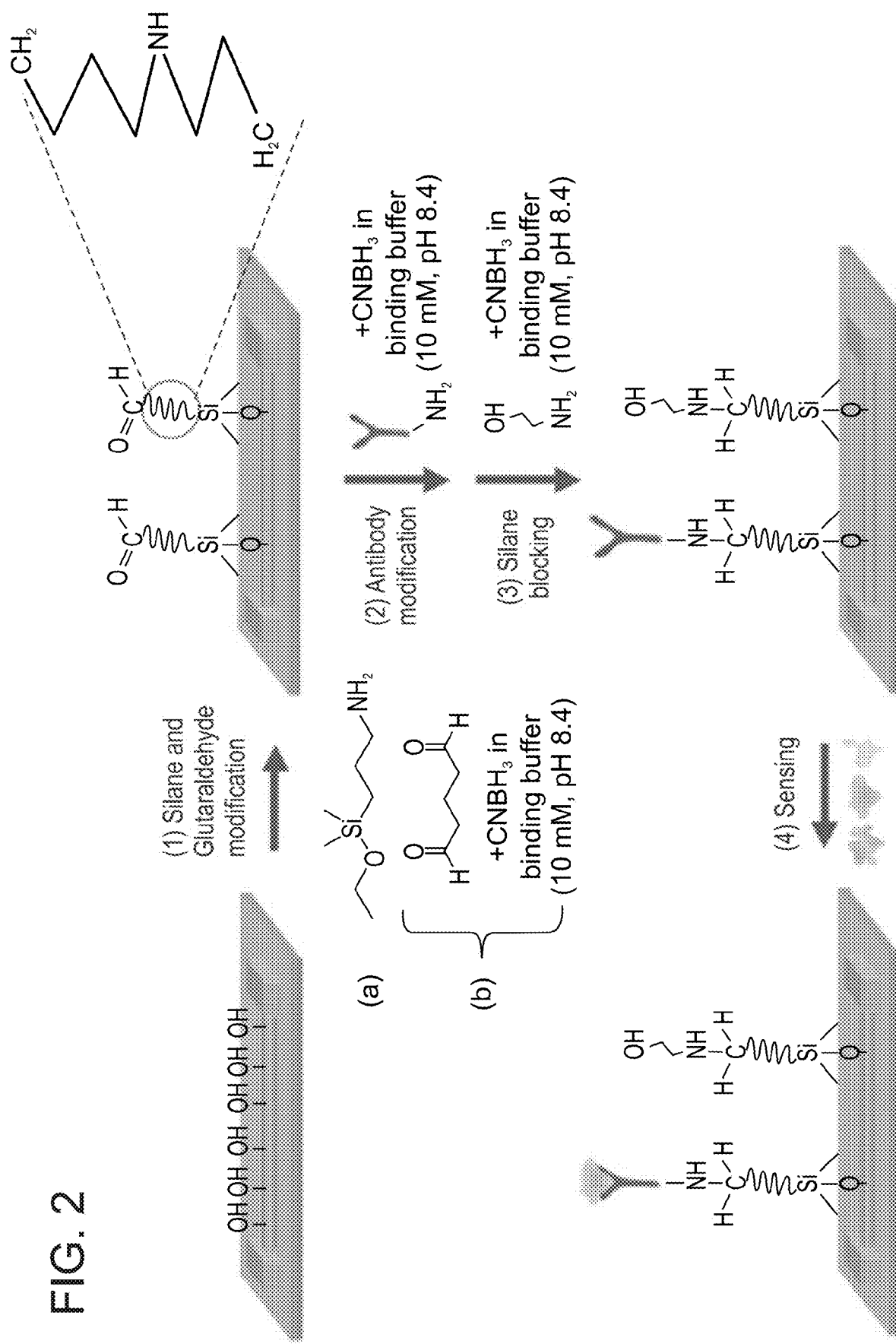
Figure 3:
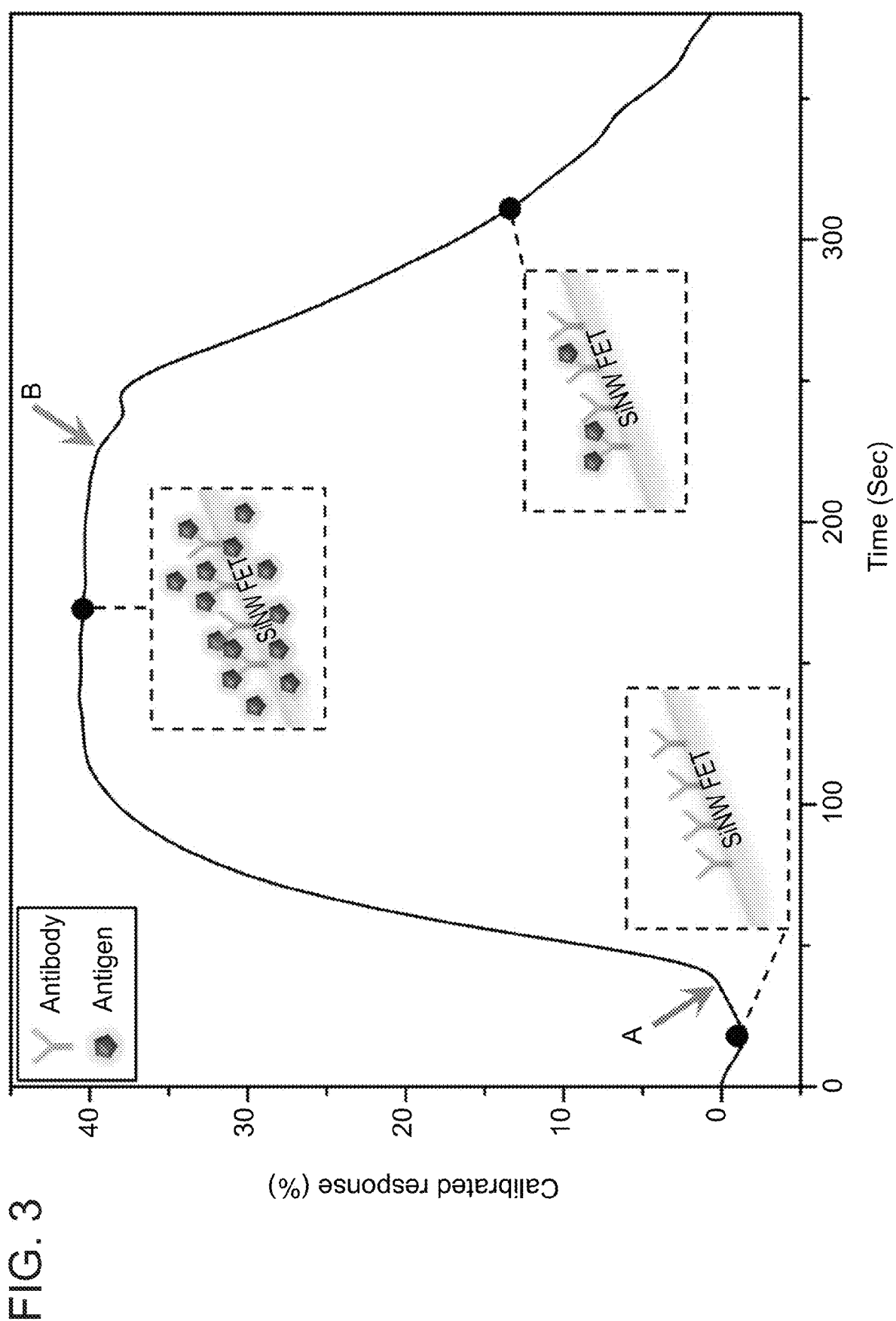
Figure 4:
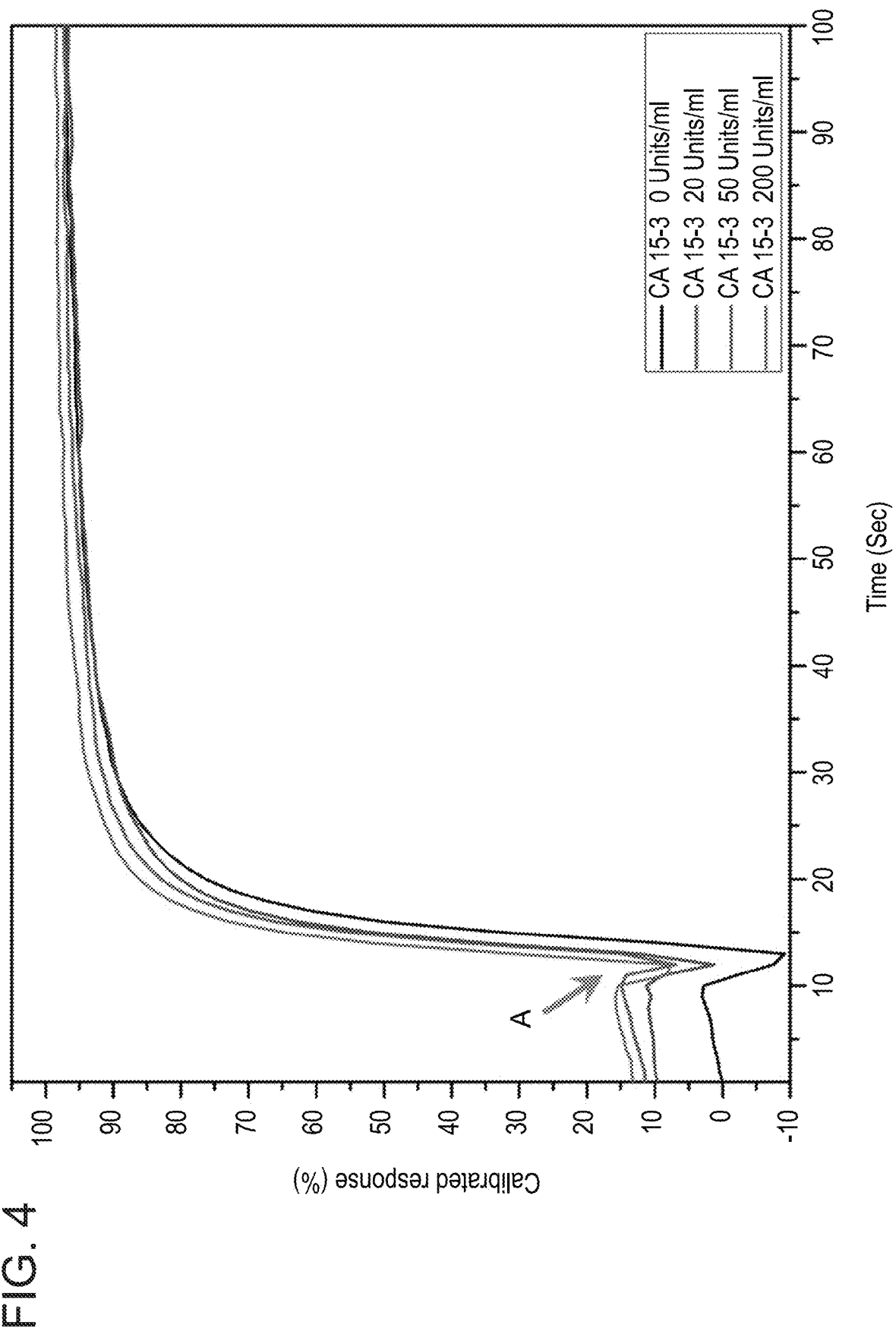
Figure 5:
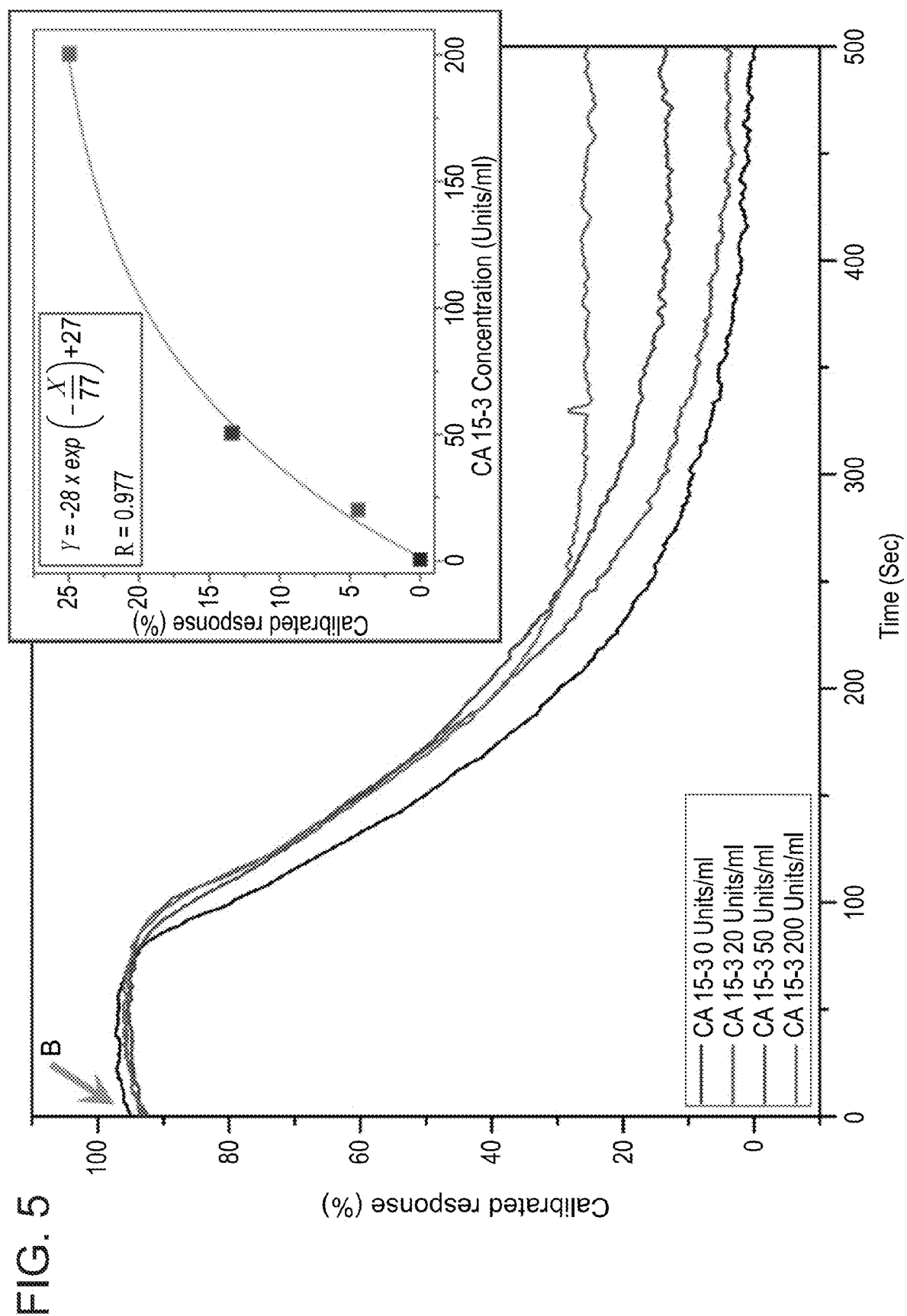
Figure 6:
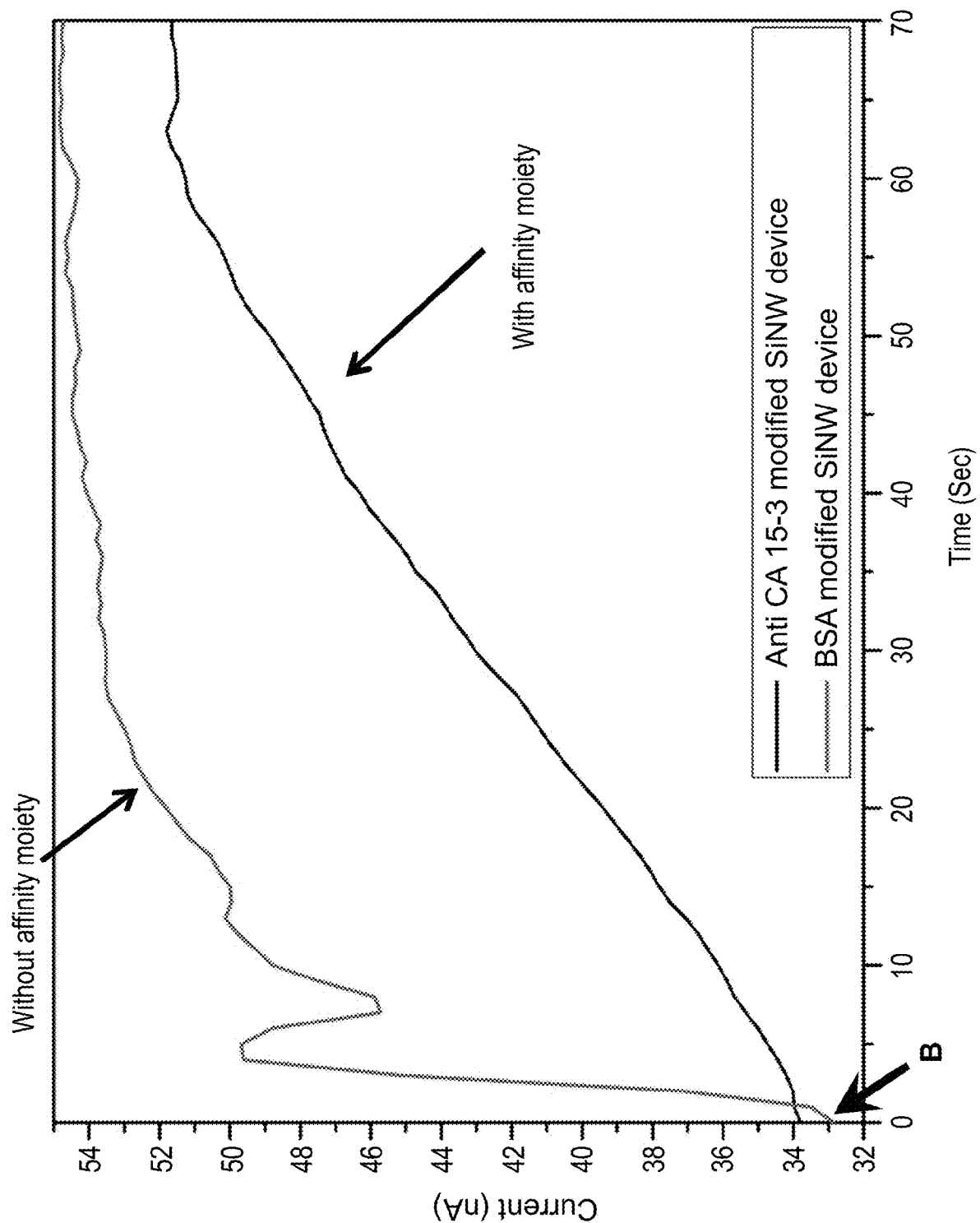
Figure 7:
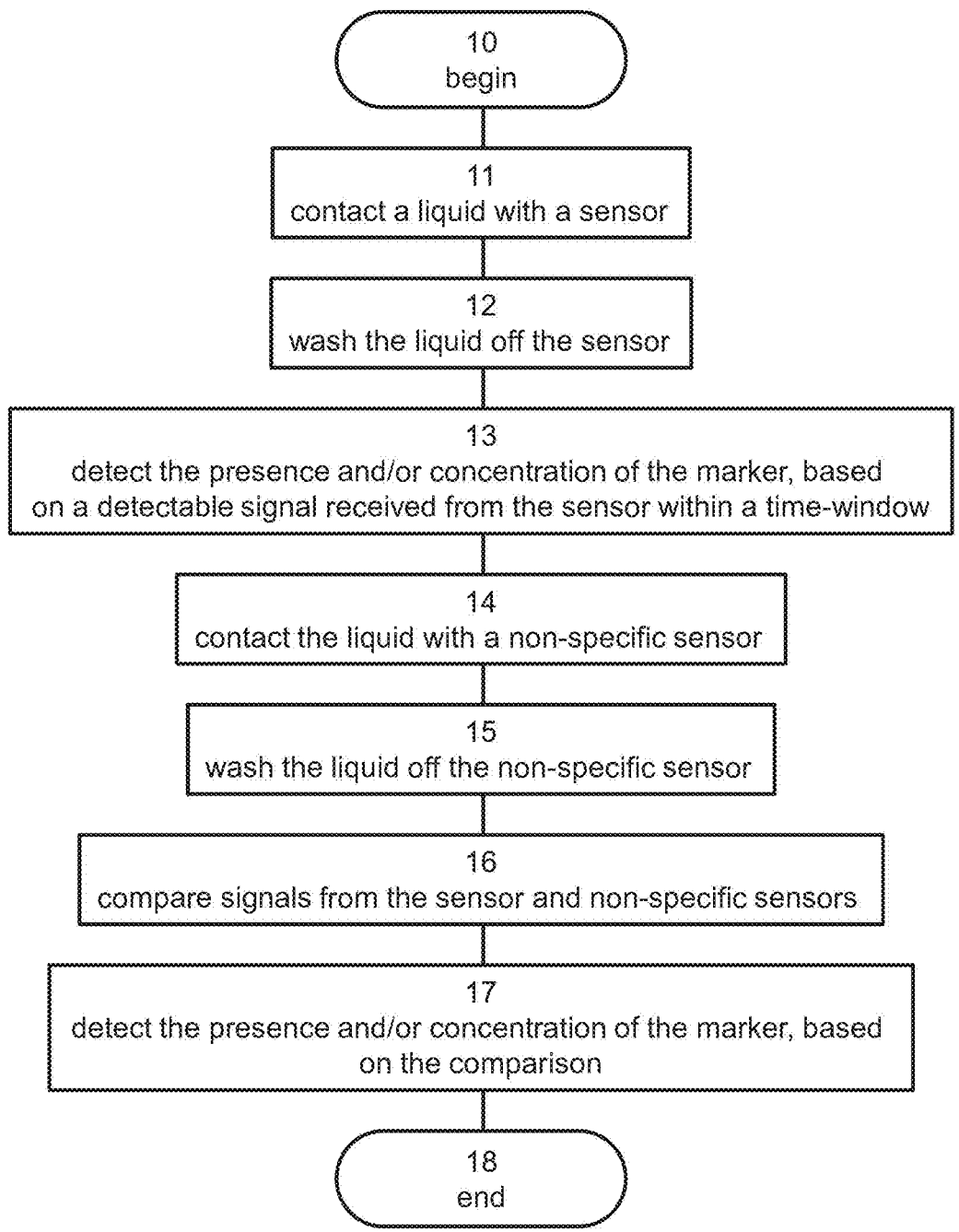
Figure 8A:
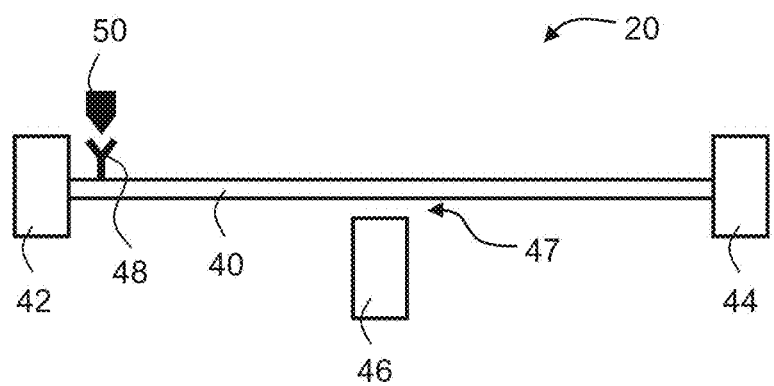
Figure 8B:
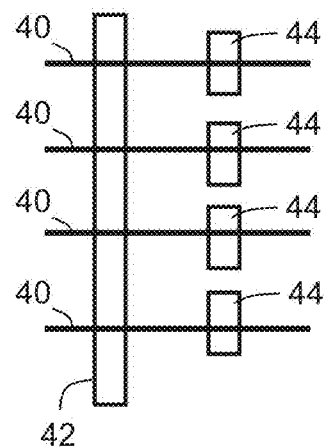
Figure 9:
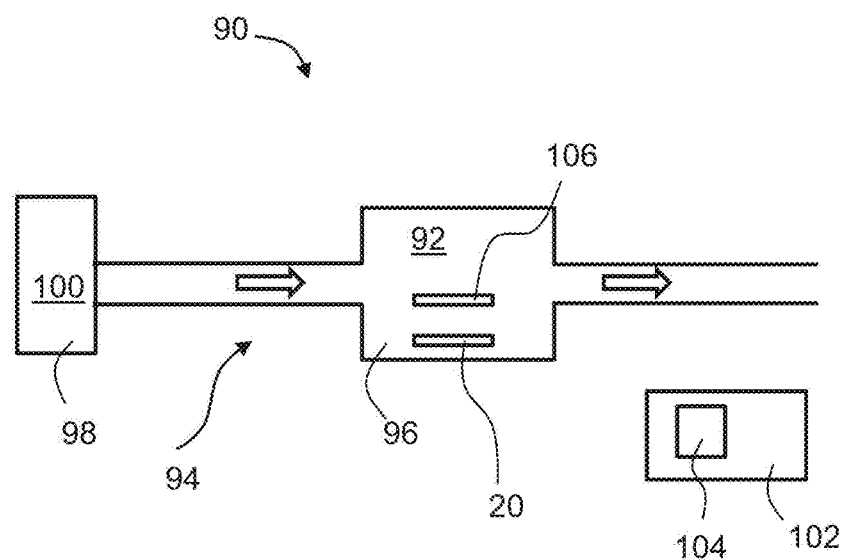
Figure 10:
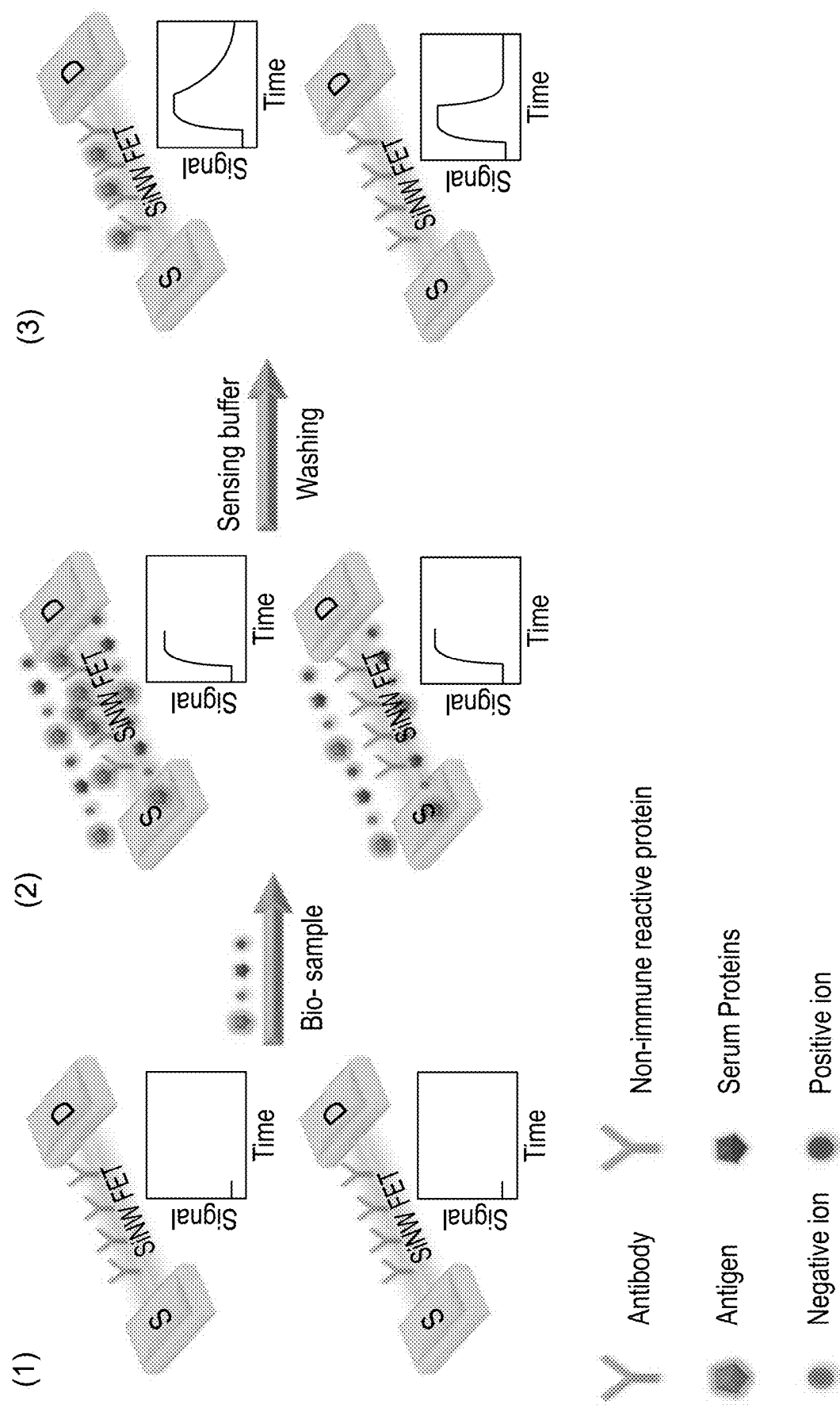
Figure 11:
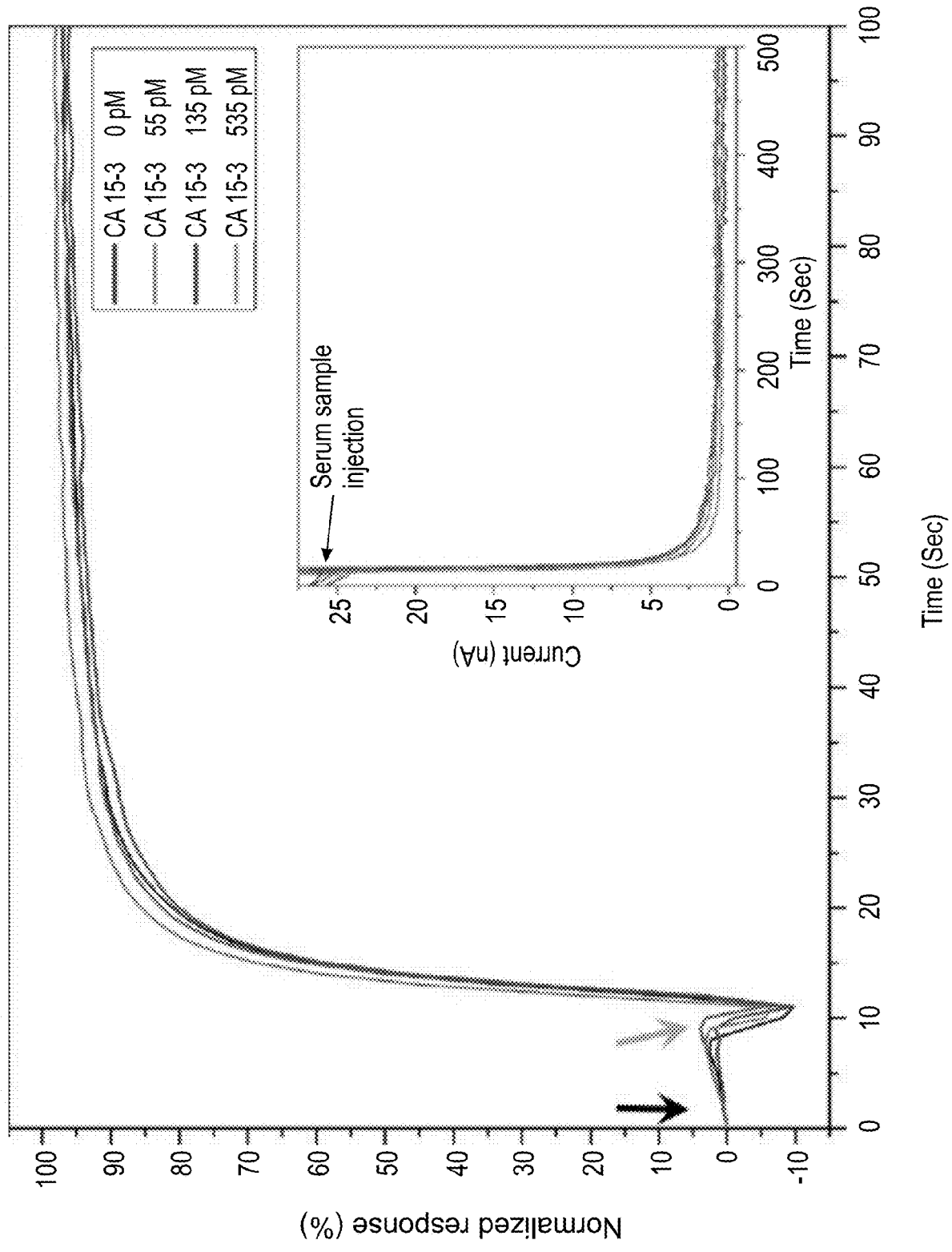
Figure 12:
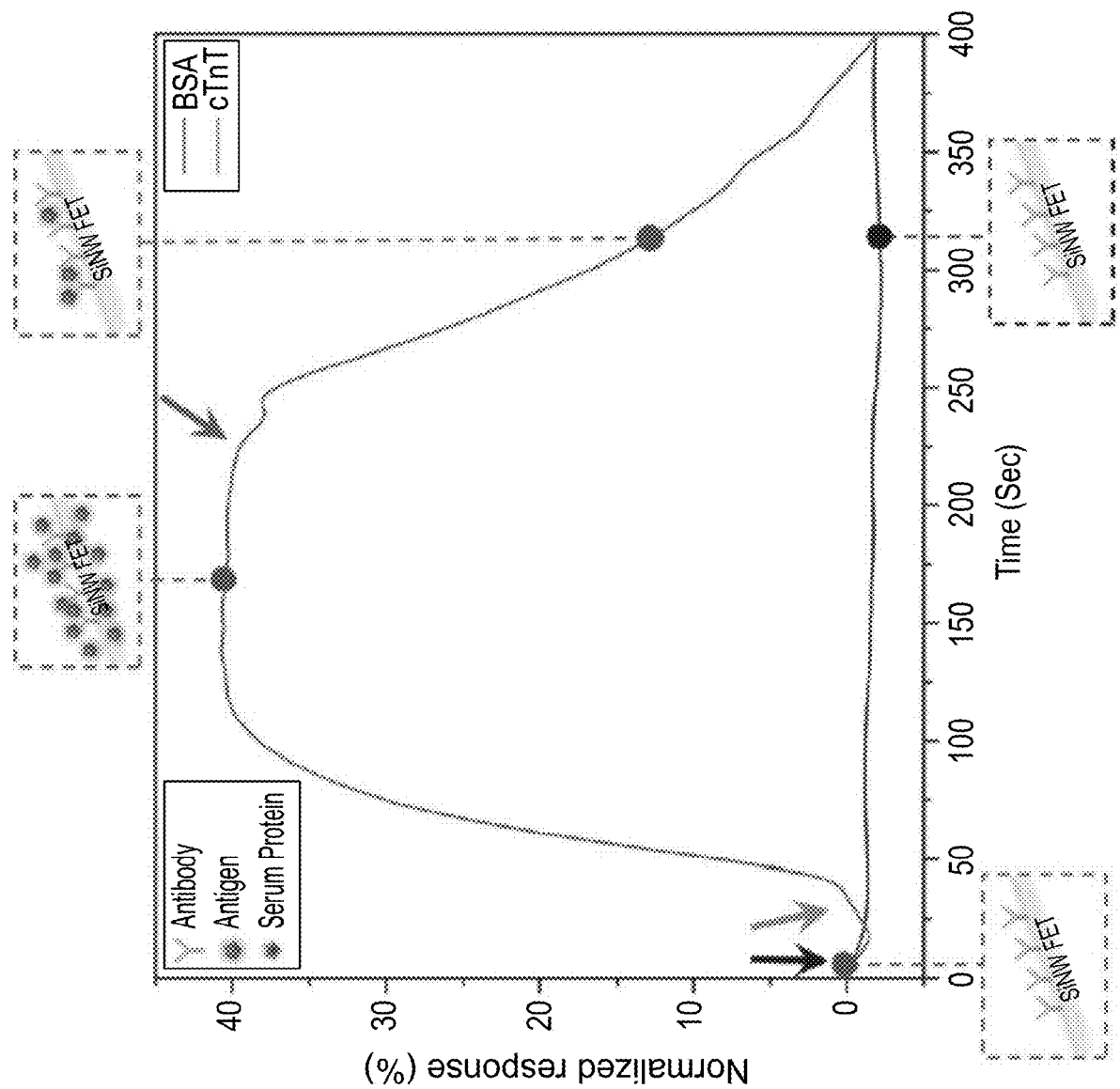
Figure 13:
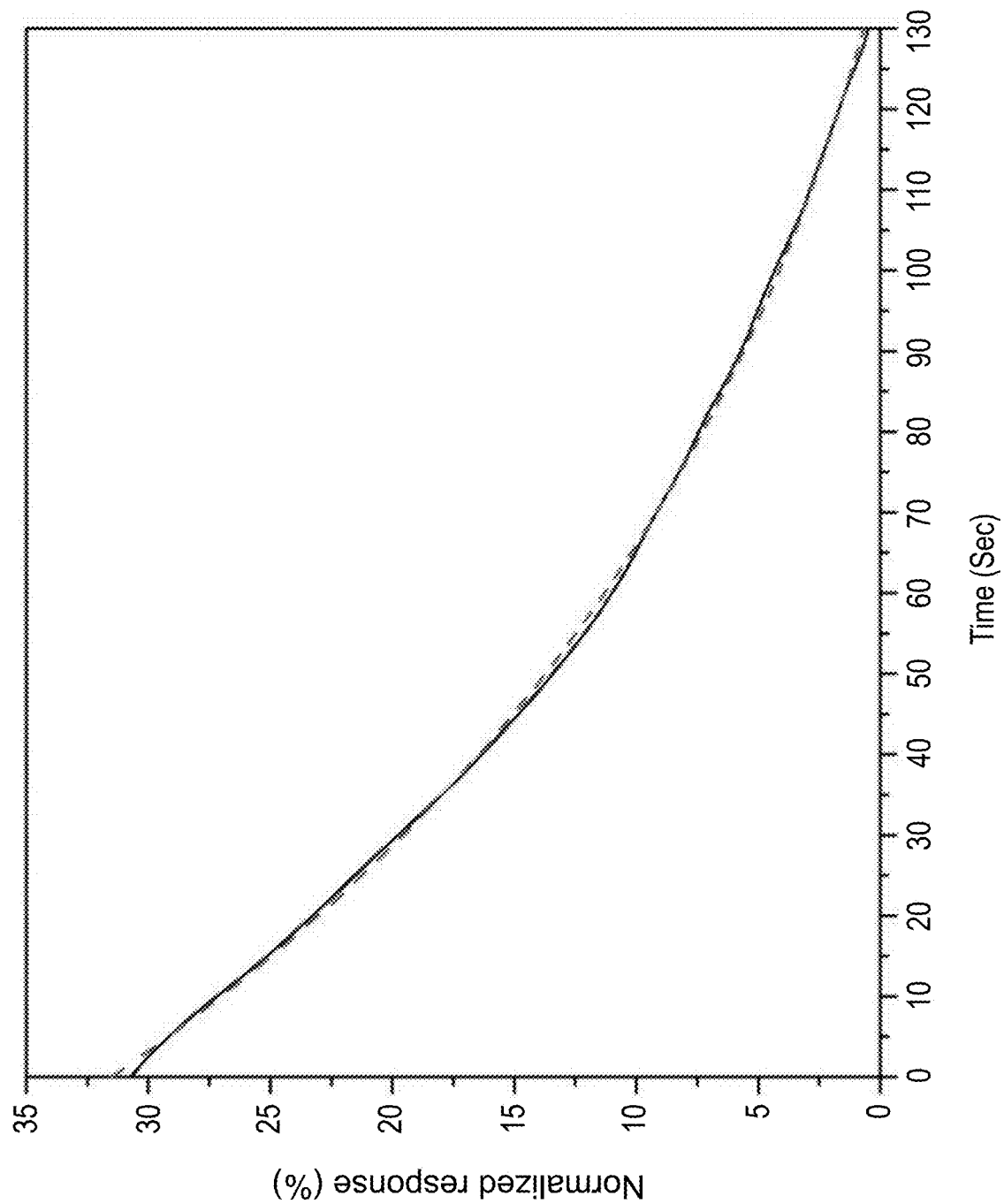
Figure 14A:
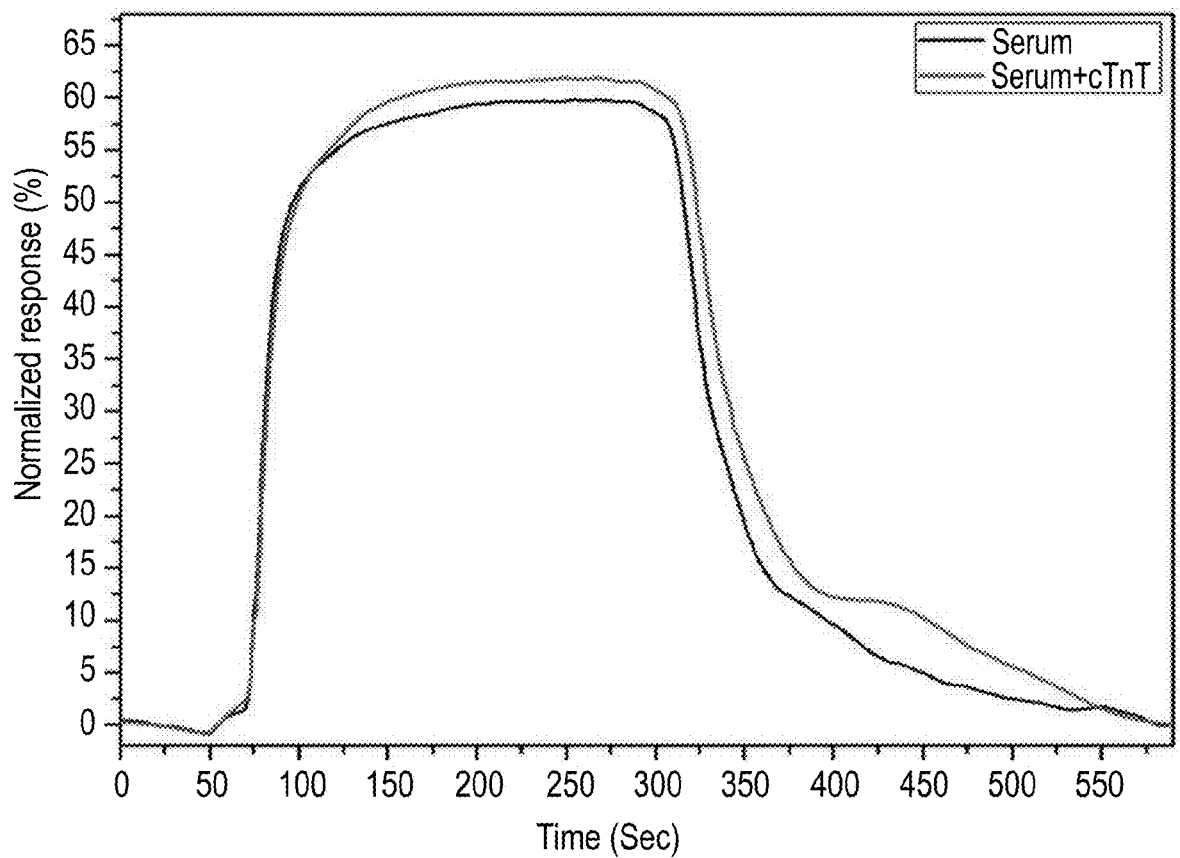
Figure 14B:
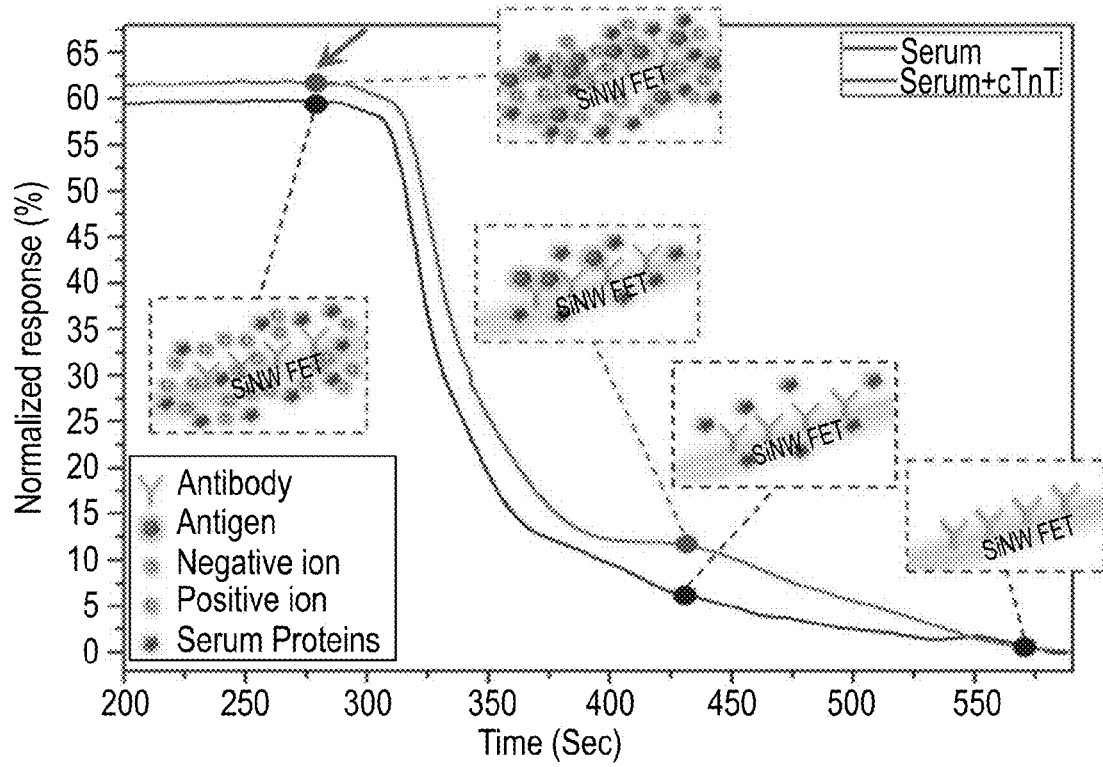
Figure 15:
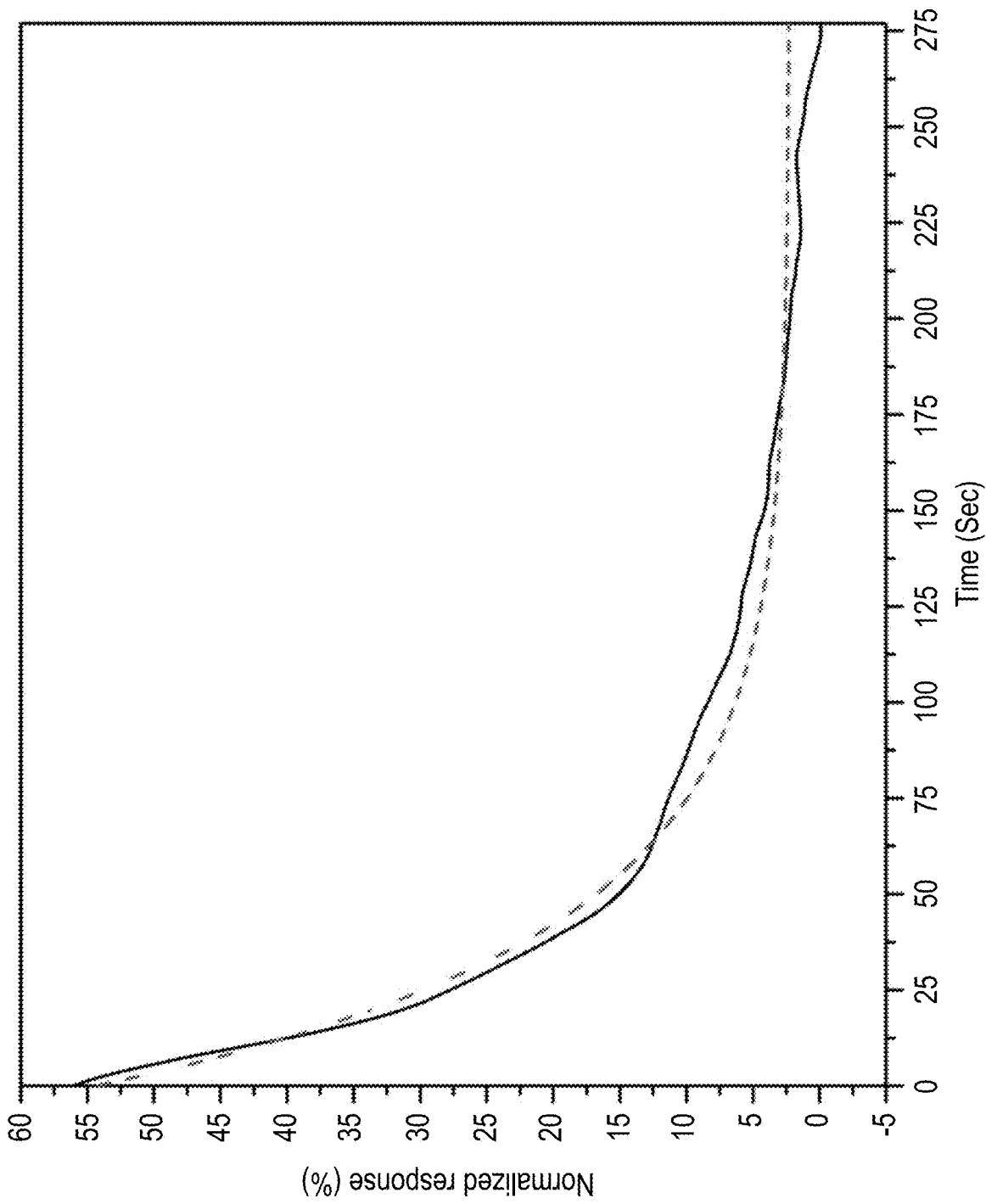
Figure 16:
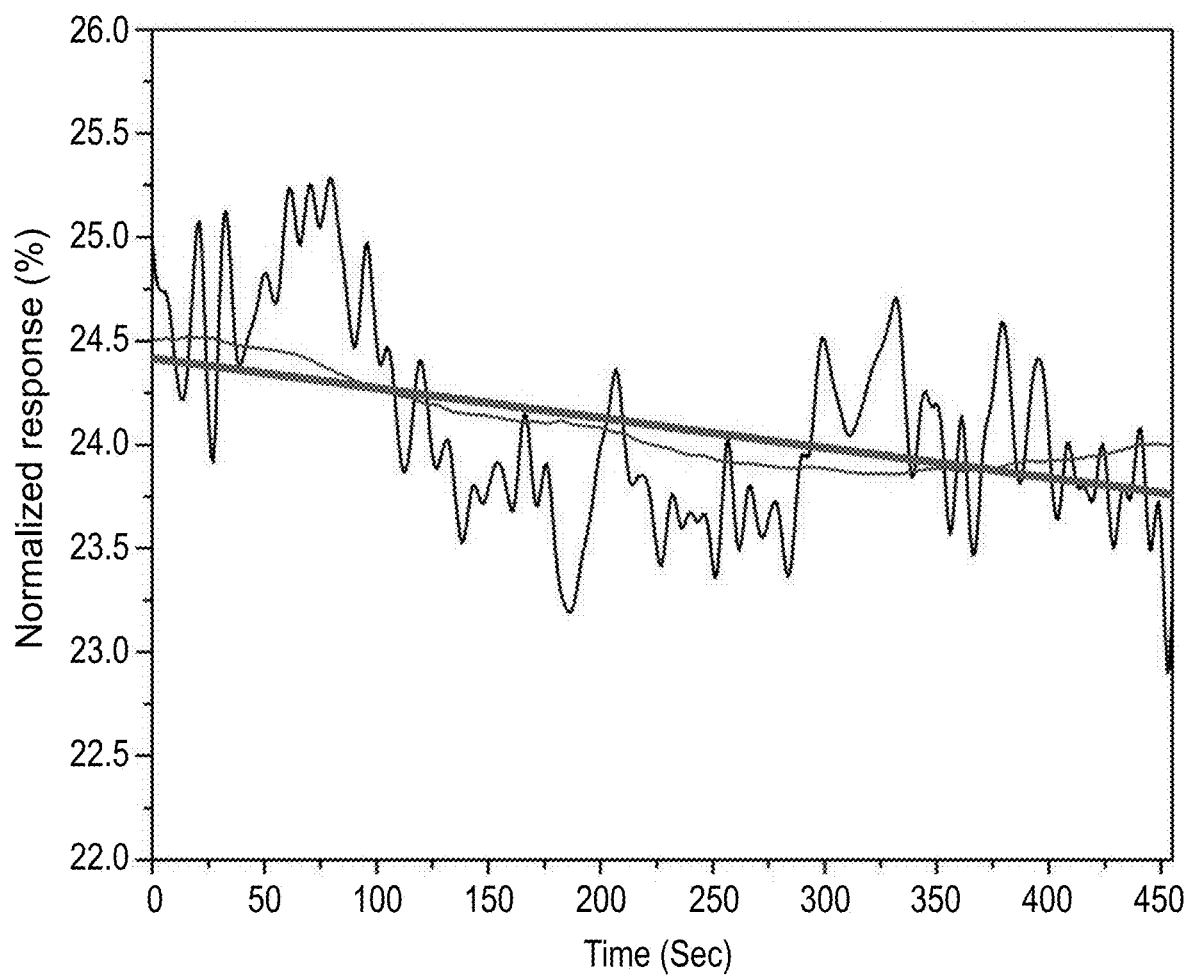
Figure 18:
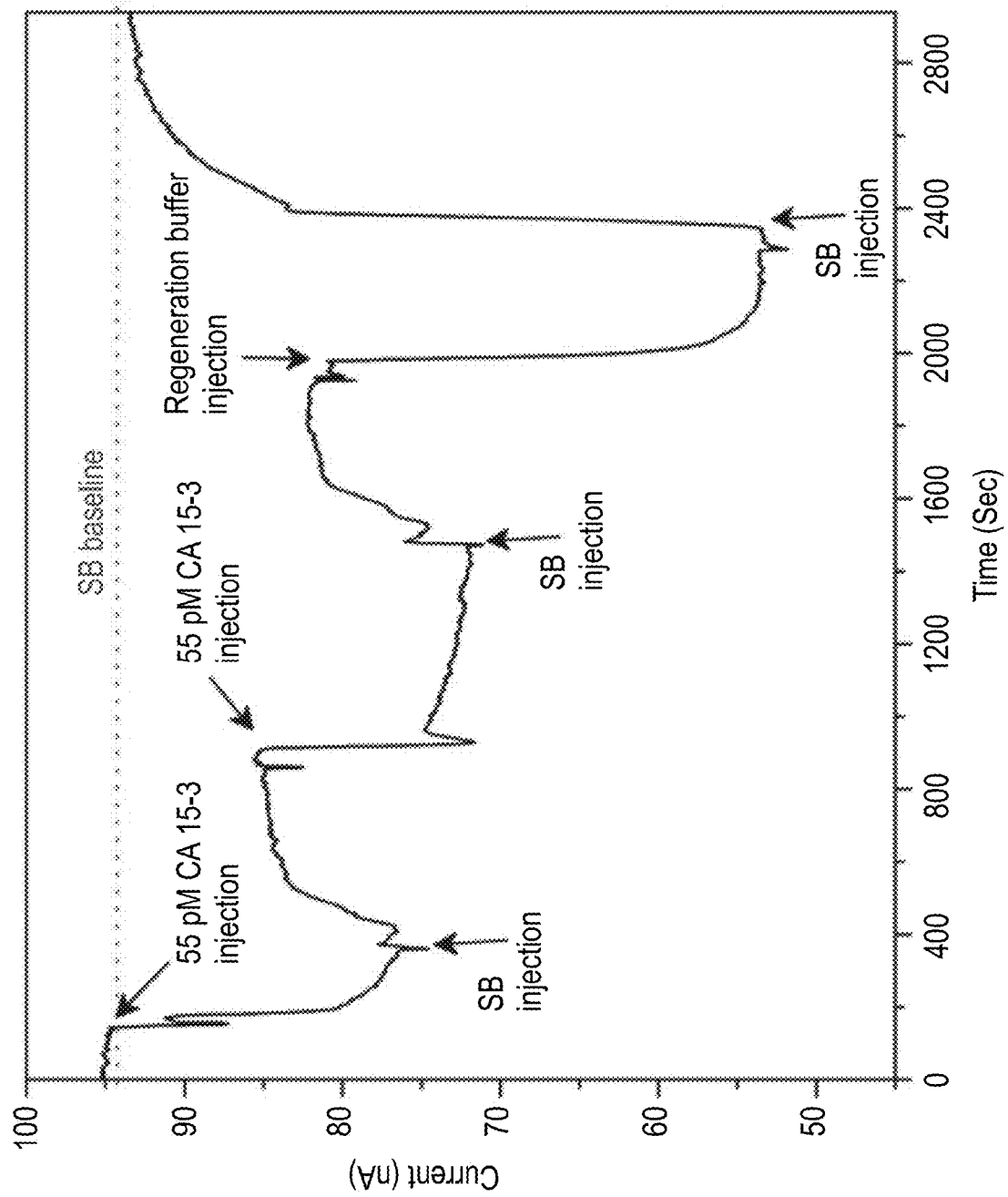
Figure 19A:
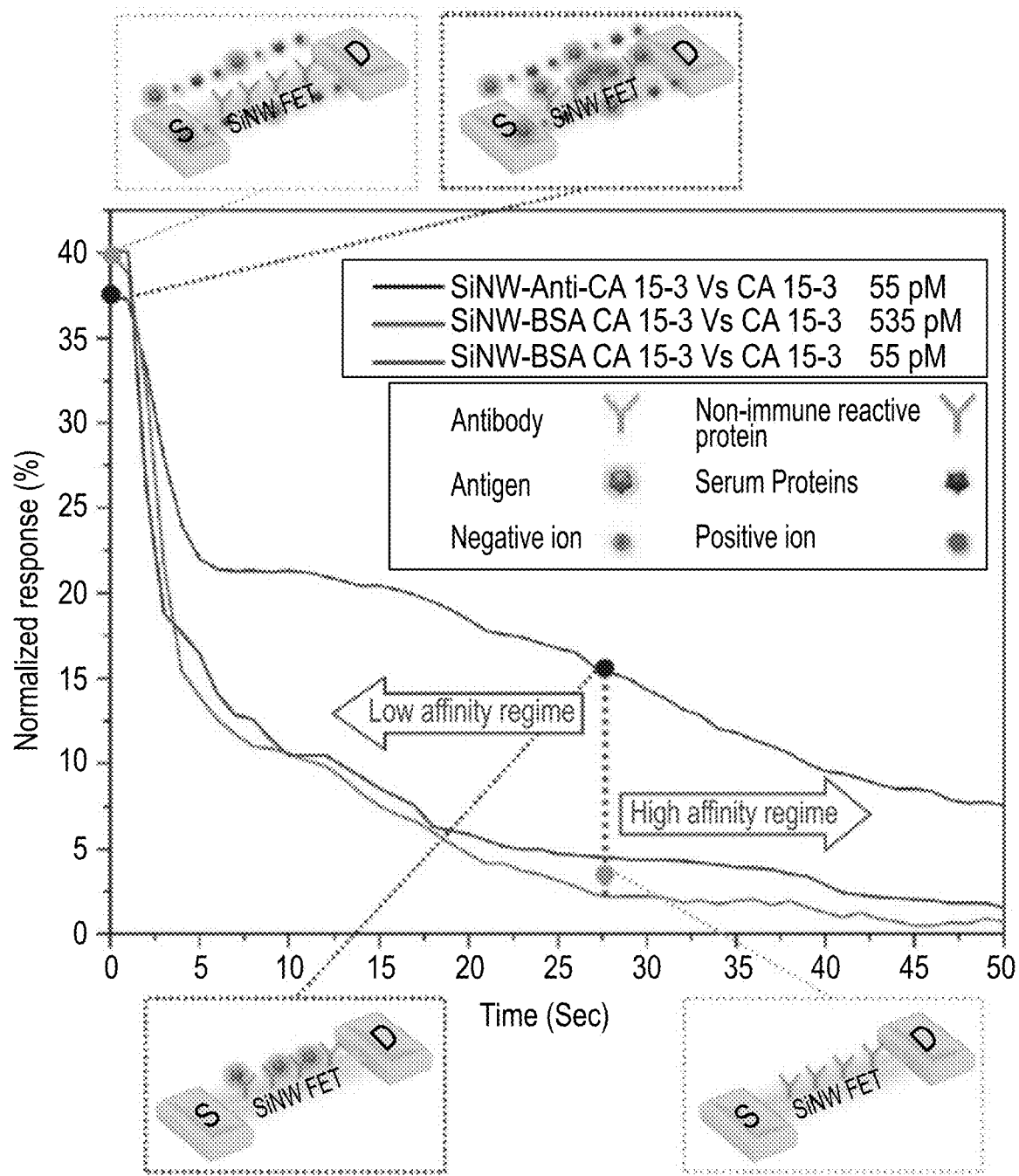
Figure 19B:
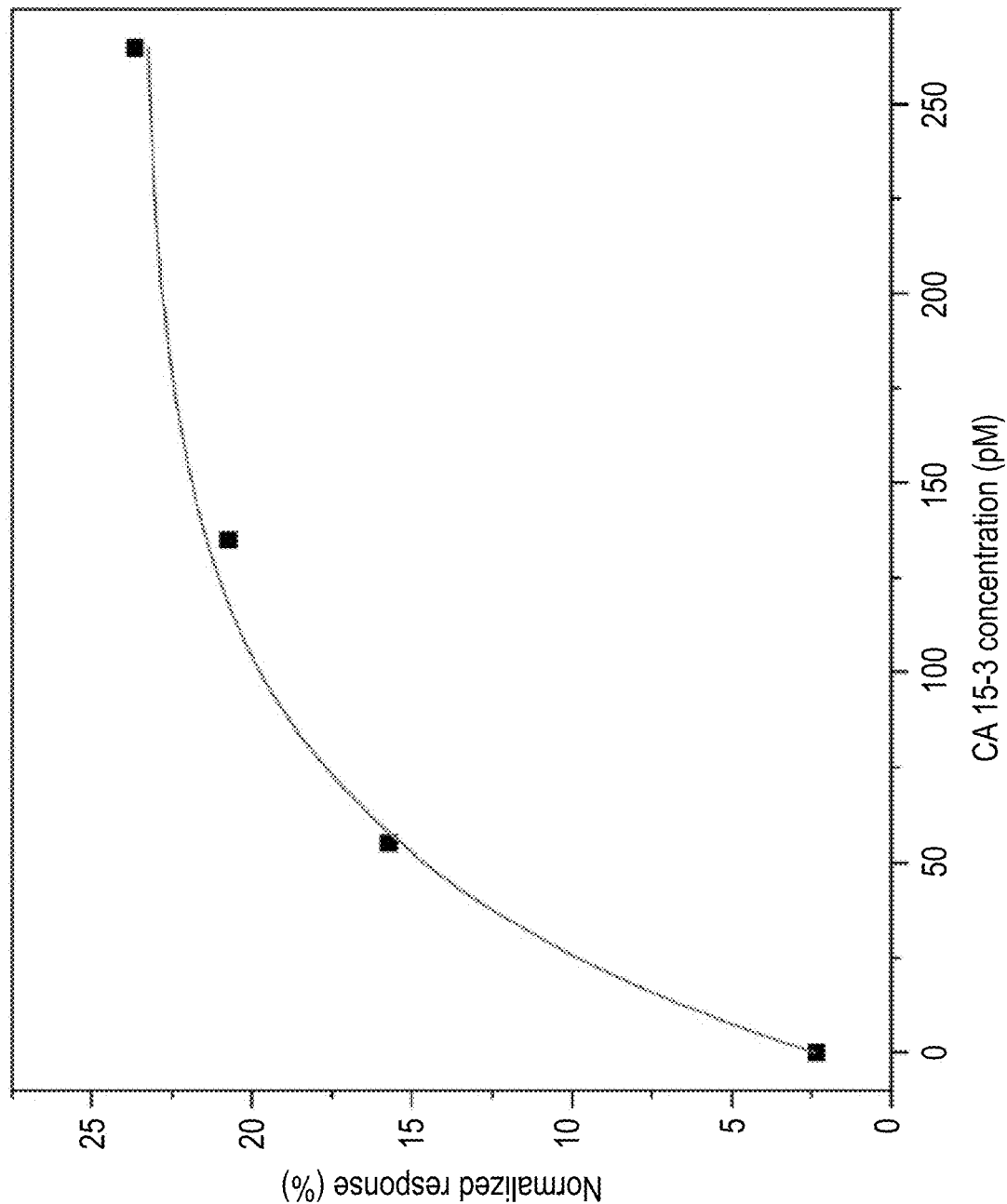
Figure 20:
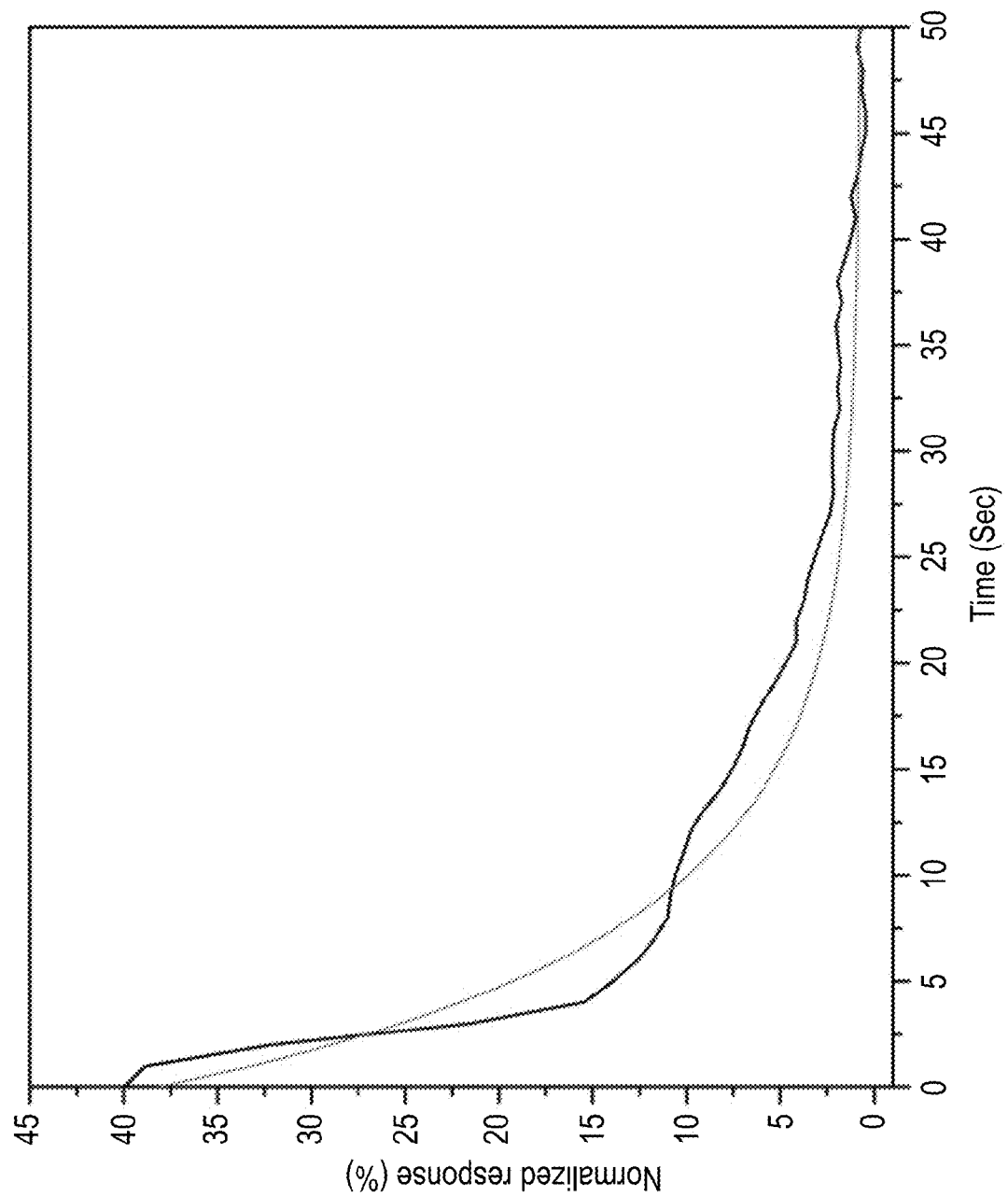
Figure 21:
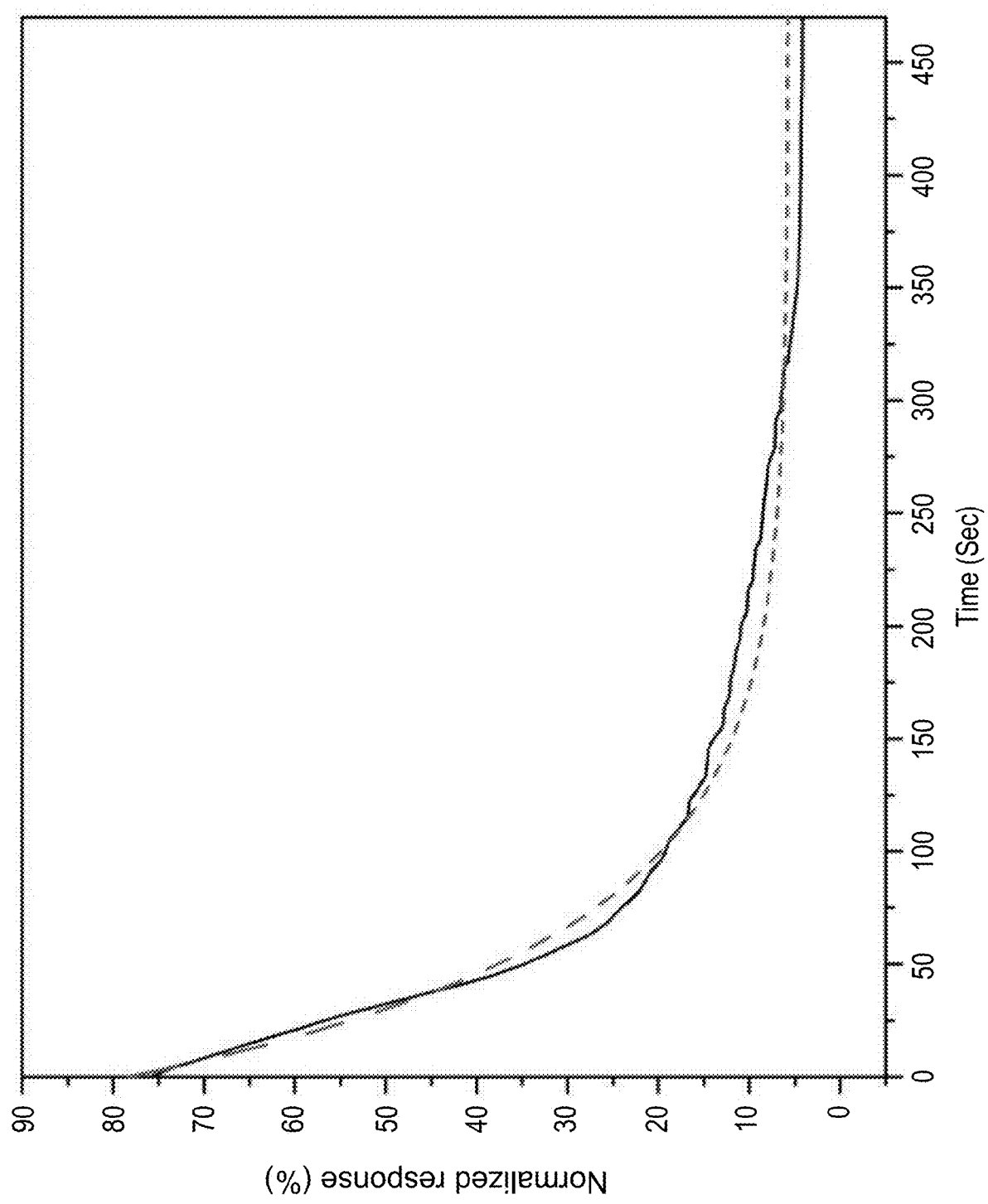
Figure 22A:
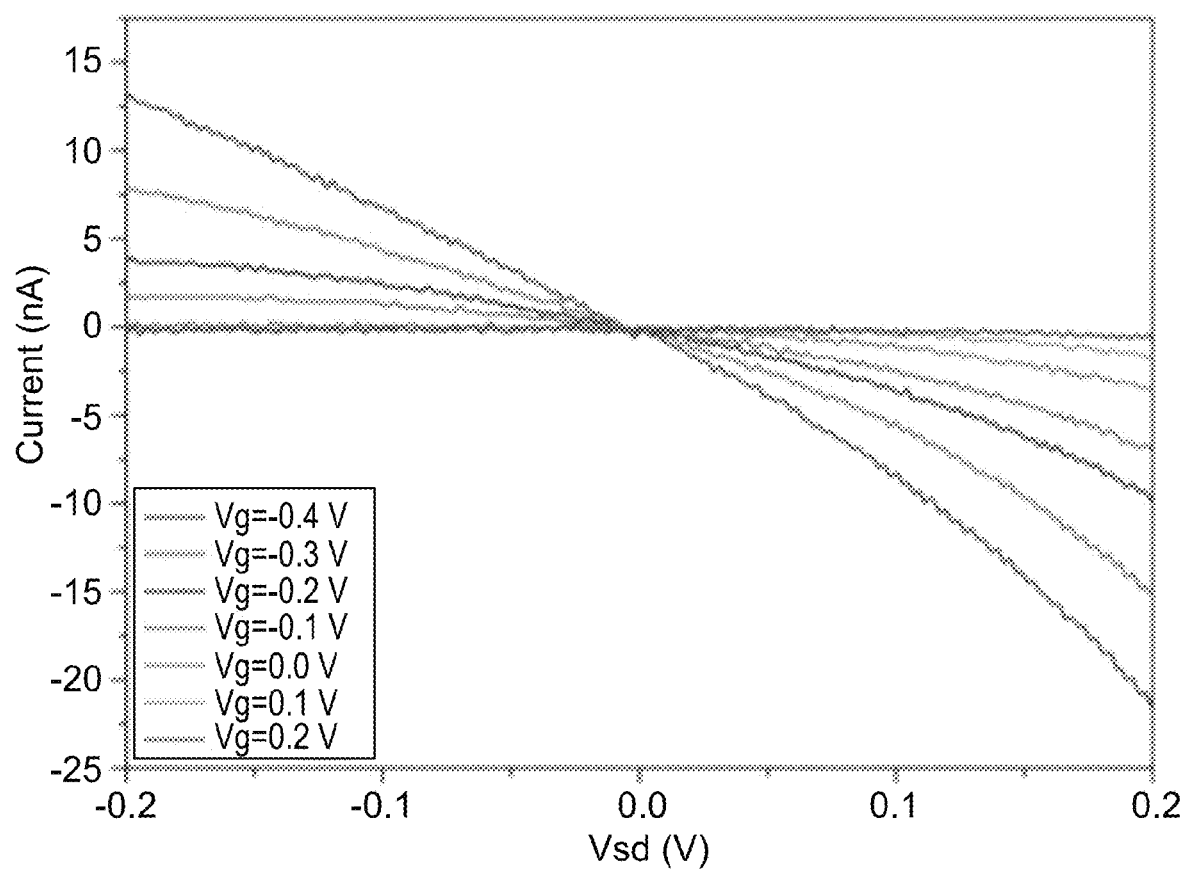
Figure 22B:
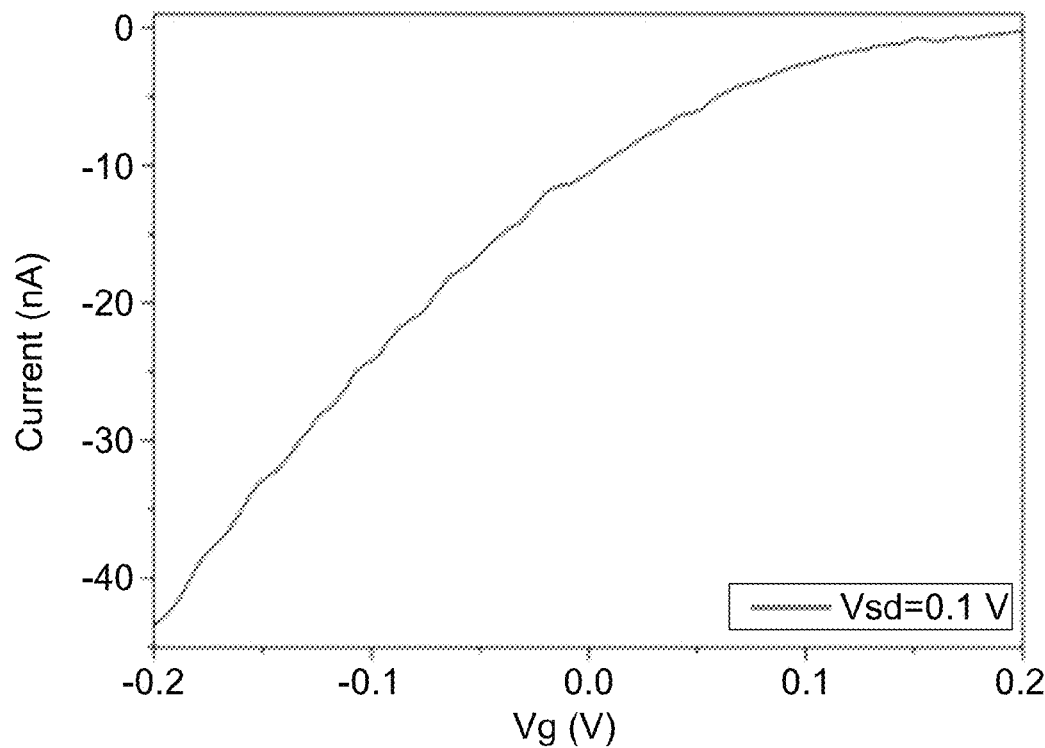
Figure 23A:
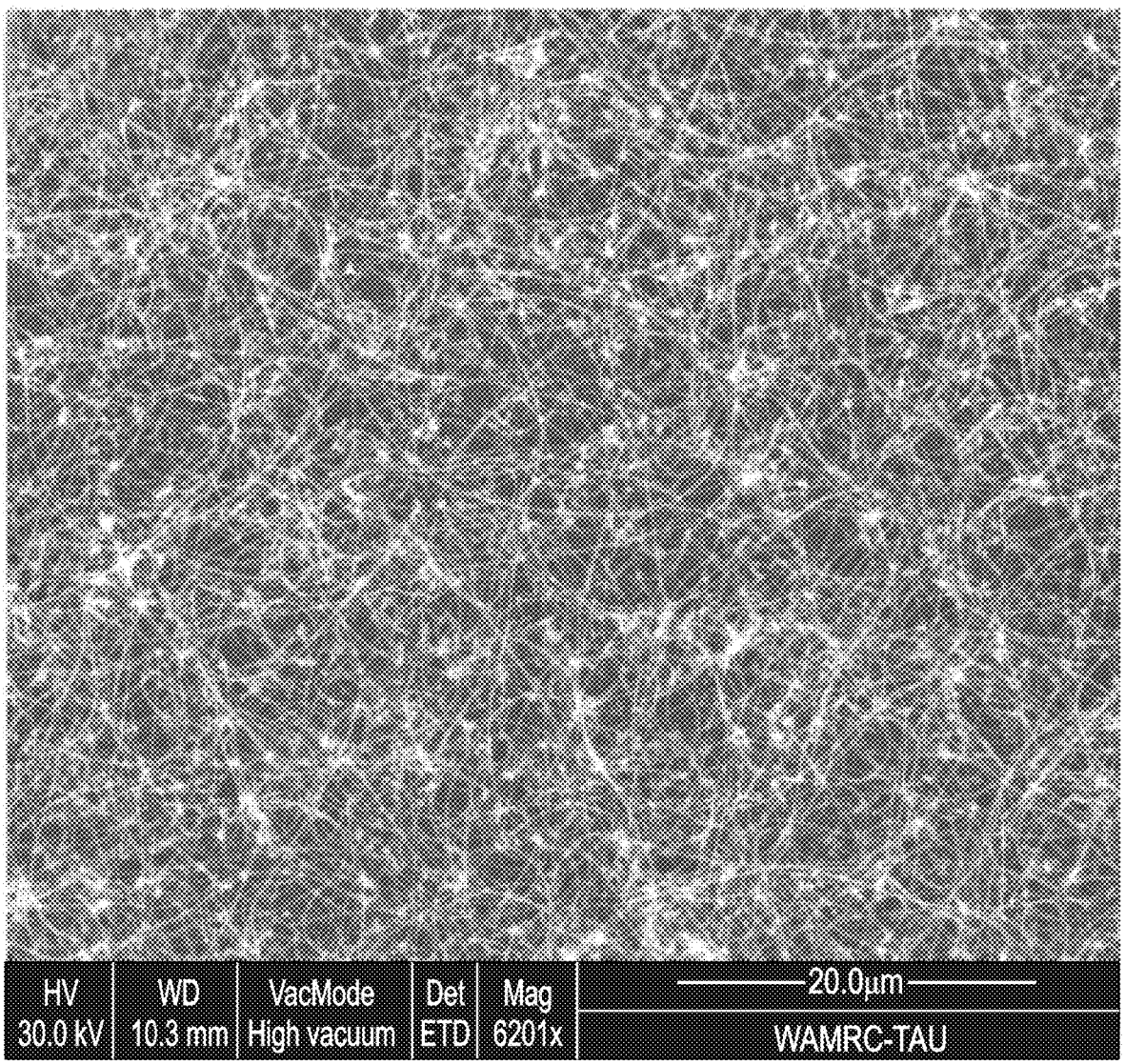
Figure 23B:
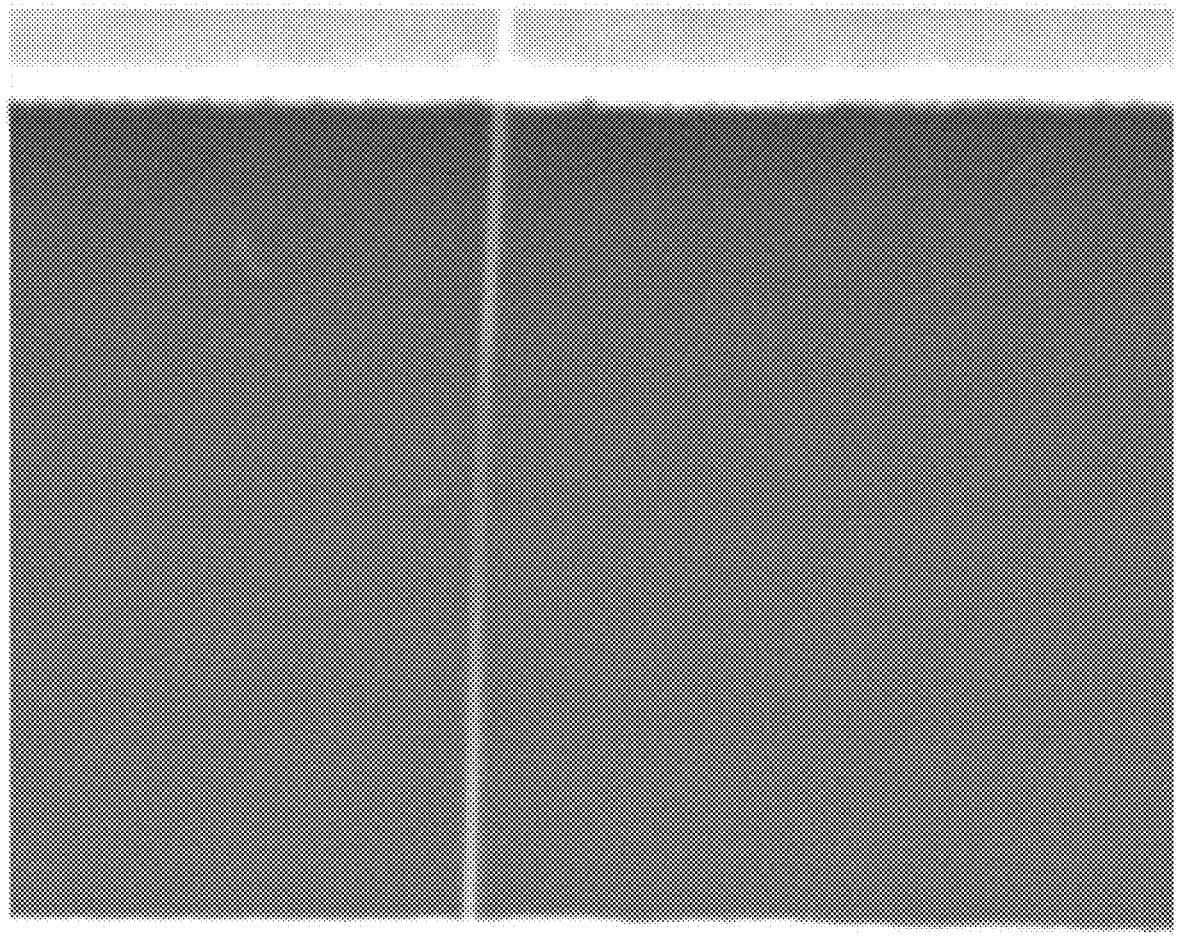

FIGS. 1A-G are images (FIGS. 1A and 1B) and schematic illustrations of a fabrication process (FIGS. 1C-G) of a 20 nm diameter P-type silicon nanowires (SiNW) FET device, according to some embodiments of the present invention;

FIG. 2 is a schematic illustration of a process for the modification of SiNW FET device with antibodies, according to some embodiments of the present invention;

FIG. 3 shows an exemplary response calibration curve of an antibody-modified SiNW FET, upon introducing of an antigen-containing buffer, following by introducing a washing buffer into a fluidic system containing the a plurality of SiNW FET, as obtained in experiments performed according to some embodiments of the present invention;

FIG. 4 shows a calibrated response of an antibody-modified SiNW FET, in a bio-sample, as obtained in experiments performed according to some embodiments of the present invention;

FIG. 5 shows a response calibration curve in the presence of the bio-sample of FIG. 4, but after initiation of a washing operation, according to some embodiments of the present invention;

FIG. 6 shows two response calibration curves obtainable in the presence of a bio-sample, after the initiation of a washing operation, as obtained in experiments performed according to some embodiments of the present invention;

FIG. 7 is a flowchart diagram schematically illustrating of a method suitable for detecting a presence and/or concentration of a biomarker in a biological liquid, according to some embodiments of the present invention;

FIGS. 8A and 8B are schematic illustrations of sensors suitable for use according to some embodiments of the present invention;

FIG. 9 is a schematic illustration of a system for detecting a presence and/or concentration of a marker, e.g., biomarker in a liquid e.g., biological liquid, according to some embodiments of the present invention;

FIG. 10 is a schematic illustration describing an operation principle of a detection of an antigen from antibody-modified SiNW FET sensing devices, according to some embodiments of the present invention;

FIG. 11 shows normalized association response of a representative anti-CA 15-3 immobilized SiNW FET sensing device against various concentrations of the target antigen CA 15-3 in unprocessed serum samples, as obtained during experiments performed according to some embodiments of the present invention;

FIG. 12 shows normalized electrical response of a representative anti-troponin antibody-modified SiNW FET sensing device to the association and dissociation of its specific antigen troponin T under low-ionic strength conditions, as obtained during experiments performed according to some embodiments of the present invention;

FIG. 13 shows anti-troponin antibody dissociation curve in serum, together with a fit, under slow-flow conditions, as obtained during experiments performed according to some embodiments of the present invention;

FIGS. 14A and 14B show results of a comparison between dissociation kinetics of troponin T antigen-containing serum sample and a control troponin T-free serum sample, as obtained during experiments performed according to some embodiments of the present invention;

FIG. 15 shows the serum dissociation curve, together with a fit, under slow-flow conditions, as obtained during experiments performed according to some embodiments of the present invention;

FIG. 16 shows anti-CA 15-3 antibody dissociation curve in serum, together with a fit, under slow-flow conditions, as obtained during experiments performed according to some embodiments of the present invention;

FIGS. 17A-D show concentration-dependent sensing of CA 15-3 antigen in unprocessed serum samples, at a flow rate of 1 chamber-volume exchange per minute, as obtained during experiments performed according to some embodiments of the present invention;

FIG. 18 shows regeneration curve of a CA 15-3 antigen from its antibody-modified nanowire device, as obtained during experiments performed according to some embodiments of the present invention;

FIGS. 19A and 19B demonstrate multiplex single-chip differential detection of the CA 15-3 antigen using specific and nonspecific chemically modified SiNWs FET devices, at a flow rate of 330 chamber-volumes per minute, as obtained during experiments performed according to some embodiments of the present invention;

FIG. 20 shows antigen-free serum dissociation curve under fast-flow conditions, together with a fit, as obtained during experiments performed according to some embodiments of the present invention;

FIG. 21 shows antigen-free untreated blood dissociation curve under slow-flow conditions, together with a fit, as obtained during experiments performed according to some embodiments of the present invention;

FIGS. 22A and 22B show electrical characterization of a p-type SiNW FET nanodevices under water-gate configuration, as obtained during experiments performed according to some embodiments of the present invention; and FIGS. 23A and 23B are Scanning Electron Microscope (SEM) images of the SiNWs obtained during experiments performed according to some embodiments of the present invention.

DESCRIPTION OF SPECIFIC EMBODIMENTS OF THE INVENTION

The present invention, in some embodiments thereof, relates to sensing and, more particularly, but not exclusively, to a methods and system for detecting a marker, such as, but not limited to, a biomarker, in a liquid, such as, but not limited to, biological liquid. Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

The present inventors have designed a sensing system and method, which is usable for sensing and optionally and preferably monitoring the presence, and more preferably amount, of a marker in a liquid. The sensing system and method can be used for multiplex real-time monitoring of many types of markers in many types of liquids.

The sensing system of the present embodiments can be used in many applications, including without limitation, chemical applications, genetic applications, biochemical applications, pharmaceutical applications, biomedical applications, medical applications, radiological applications and environmental applications.

For medical applications, the sensing system and method of the present embodiments is suitable for monitoring presence, and more preferably level, of a biomarker in a biological liquid, such as a physiological solution.

For environmental applications the sensing system and method of the present embodiments is suitable for monitoring presence, and more preferably level, markers indicative of the presence or level of hazardous materials in a liquid, such as, but not limited to, water pollutants, chemical agents, biological organisms or radiological conditions in water.

The liquid can be a liquid that comprise blood product, either whole blood or blood component. For example, the liquid can be a blood sample. The liquid can comprise other body liquids, including, without limitation, saliva, cerebral spinal fluid, urine and the like. The liquid can be a buffer or a solution, such as, but not limited to, nucleic acid solutions, protein solutions, peptide solutions, antibody solutions and the like. Also contemplated are liquids containing one or more biological and chemical reagents such as, but not limited to, oxidizing agents, reducing agents, enzymes, receptor ligands, extracellular components, metabolites, fatty acids, steroids, and the like. A representative list of liquids in which the system and method of the present embodiments can sense a marker, include, without limitation, water, salt water, urine, blood, sperm, saliva, mucous, catemenial fluid, lymphatic fluid, cerebral spinal fluid, vaginal exudate, pus, vomit, perspiration, and inorganic liquids, including, without limitation, petroleum liquids, oils or other lubricants.

According to some embodiments of the invention, a liquid, e.g., biological liquid having a marker, e.g., a biomarker, is introduced into a fluidic system that comprises a sensor having an immobilized affinity moiety interacting with the marker and being configured to generate a detectable signal responsively to the interaction. The interaction is optionally and preferably being characterized by a $K_D$ which is equal or less than $10^{-5}$ M or a $K_D$ which is equal or less than $10^{-6}$ M or a $K_D$ which is equal or less than $10^{-7}$ M or a $K_D$ which is equal or less than $10^{-8}$ M or a $K_D$ which is equal or less than $10^{-9}$ M or a $K_D$ which is equal or less than $10^{-10}$ M. The marker from the liquid binds selectively to the affinity moiety. Background components, which may include objects of any type, such as, but not limited to, salts and bio-molecules, may be adsorbed non-specifically to the sensor's surface.

After the selective adsorption of the marker to the sensor's surface, the sensor is washed with a washing buffer. This results in a desorption of background components from the surface of the sensor. Since the interactions between the marker and the affinity moiety are stronger than the interaction of the background components with the surface of the sensor, the background components leave the sensor's surface much faster than the marker. The desorption kinetic of the marker from the sensor are preferably detected after all or most of the background components are washed out.

While the embodiments below are described with a particular emphasis to biomarkers in a biological liquid, it is to be understood that other types of markers and other types liquid are also contemplated.

The system of the present embodiments optionally and preferably provides a direct analysis of bio-samples on a single chip. The system of the present embodiments can selectively detect specific low abundant biomarkers, while removing unwanted components (salts, bio-molecules, proteins, cells, etc.). Preferably, the analysis is performed without performing at least one of, or more preferably without any of: centrifugation, desalting and affinity columns, since such operations are known to be time-consuming. In some embodiments of the present invention the analysis process is performed in less than 15 minutes or less than 10 minutes or less than 5 minutes.

In some embodiments of the present invention the amount of the biomarker in the bio-sample is also measured. This can be done, for example, by providing a system in which some sensors include the affinity moiety and some do not include the affinity moiety. The desorption from the sensors that do not include the affinity moiety is defined as a background. The desorption kinetic of the biomarker from sensors that include the affinity moiety are optionally and preferably compared to this background, and the amount of the biomarker desorbed from sensors that include the affinity moiety is determined based on this comparison, for example, by subtracting the signals from each other. Since the specific absorption of the biomarkers to the surfaces is proportional to the concentration of the biomarker in the bio-sample, the desorption kinetics above background is concentration-dependent.

Reference is now made to FIG. 7 which is a flowchart diagram schematically illustrating of a method suitable for detecting a presence and/or concentration of a marker, e.g., a biomarker, in a liquid, e.g., a biological liquid, according to some embodiments of the present invention.

It is to be understood that, unless otherwise defined, the operations described hereinbelow can be executed either contemporaneously or sequentially in many combinations or orders of execution. Specifically, the ordering of the flowchart diagrams is not to be considered as limiting. For example, two or more operations, appearing in the following description or in the flowchart diagrams in a particular order, can be executed in a different order (e.g., a reverse order) or substantially contemporaneously. Additionally, several operations described below are optional and may not be executed.

The method begins at 10 and optionally and preferably continues to 11 at which the liquid is contacted with a sensor. The contact can be established by any technique known in the art. Preferably, but not necessarily, the sensor is in a fluidic system, more preferably a microfluidic system, and the liquid is introduced into the fluidic system.

FIGS. 8A and 8B are schematic illustrations of sensors suitable for the present embodiments. FIG. 8A shows a sensor 20 which comprises an immobilized affinity moiety 48. The sensor used in the technique of the present embodiments can be any potentiometric sensor that provides a detectable signal in the present of the marker or biomarker.

The detectable signal is typically produced when the electrical property (conductivity, resistivity, capacitance) of the sensor varies in response to interaction with a marker or biomarker 50. In some embodiments, the sensor is a transistor. In these embodiments, moiety 48 is optionally and preferably immobilized on a surface of the channel of the transistor.

According to some embodiments, the sensor is a nanostructure and the affinity moiety is immobilized on a surface of the nanostructure. According to some embodiments of the invention, the sensor is a transistor, having a nanostructure as a channel, wherein the affinity moiety is immobilized on a surface of the nanostructure.

According to some embodiments, the sensor is a structure that is non-nanometric. In these embodiments, all the dimensions of the structure on which the affinity moiety is immobilized (length, width and thickness) are above 1000 nm, or above 10 µm, or above 100 µm, or above 1 mm.

According to some embodiments of the invention, the sensor is a transistor, having a non-nanometric structure as a channel, wherein the affinity moiety is immobilized on a surface of the nanostructure.

According to some embodiments of the invention, the transistor is a field-effect transistor (FET).

When the sensor comprises a transistor (e.g., a FET) and the affinity moiety is immobilized on the channel of the transistor, a change in the electrical property of the channel can induce a change in the characteristic response of the transistor to the gate voltage (e.g., the source-drain current as a function of the gate voltage), which change can be detected and analyzed.

FIG. 8A illustrates an embodiment in which sensor 20 comprises a structure 40, such as, but not limited to, as nanostructure, wherein the affinity moiety 48 is immobilized on a surface of structure 40.

Affinity moiety 48 is effective to react (e.g., bind) specifically to a marker or biomarker 50 in the liquid or biological liquid.

The sensor 20 is configured to generate a detectable signal, typically an electrical signal, responsively to the interaction of the affinity moiety 48 with the marker or biomarker 50.

As used herein the term "affinity moiety" refers to a molecule which binds with a predetermined affinity and preferably specificity to the marker or biomarker.

Affinity moiety 48 and marker or biomarker 50 are optionally and preferably members of an affinity pair, wherein moiety 48 is capable of reversibly or non-reversibly binding to marker or biomarker 50. The interaction between moiety 48 and marker or biomarker 50 is characterized by an affinity which is typically weaker than the characteristic affinity of a covalent bond, which, when expressed in $K_D$, typically correspond to $K_D$ of about $10^{-15}$ M. In any of the embodiments of the invention, the interaction between moiety 48 and marker or biomarker 50 is characterized by an affinity which is preferably defined by a $K_D$ that is equal or less than $10^{-5}$, or a $K_D$ that is equal or less than $10^{-6}$M, or a $K_D$ that is equal or less than $10^{-7}$M, or a $K_D$ that is equal or less than $10^{-8}$M, or a $K_D$ that is equal or less than $10^{-9}$M, or a $K_D$ that is equal or less than $10^{-10}$ M.

Methods of measuring the affinity are well known in the art and include surface Plasmon resonance and competition assays.

The affinity moiety may be naturally occurring or synthetically designed or produced.

Examples of affinity moieties include a member of an antibody-antigen (immunogenic moiety), a ligand-receptor (e.g., soluble receptor or membrane bound), a carbohydrate-lectin, an RNA-aptamer, a nucleic acid sequence complementation and the like.

According to some embodiments of the invention, the affinity moiety comprises an immunogenic moiety. According to some embodiments of the invention, the immunogenic moiety comprises an antibody or a fragment thereof. According to some embodiments of the invention, the immunogenic moiety comprises an antigen. In these embodiments, the marker is a biomarker that preferably comprises an antibody to the antigen. According to some embodiments of the invention, the affinity moiety comprises a ligand. In these embodiments, the marker is preferably a biomarker that comprises a receptor.

Moiety 48 can attached to the surface of nanostructure 40 by any technique known in the art, such as, but not limited to, the technique that is based on fragmentation of antibody-capturing units and that is described in Elnathan et al., Nano Lett 2012, 12, (10), 5245-5254, the contents of which are hereby incorporated by reference.

Moiety 48 can be attached to the surface of nanostructure 40 by means of reactive groups within moiety 48 and compatible reactive groups on the surface of nanostructure 40, directly or via a linker. Preferably the attachment is a covalent attachment. In exemplary embodiments, the linker generates a reactive amine group on the surface of the nanostructure, which is optionally subjected to reductive amination to provide an aldehyde-terminated surface that binds with moiety 48. The reactive groups on the surface of nanostructure 40 can be intrinsic or can be generated upon a treatment.

Nanostructure 40 is preferably elongated.

As used herein, a "elongated nanostructure" generally refers to a three-dimensional body which is made of a solid substance, and which, at any point along its length, has at least one cross-sectional dimension and, in some embodiments, two orthogonal cross-sectional dimensions less than 1 micron, or less than 500 nanometers, or less than 200 nanometers, or less than 150 nanometers, or less than 100 nanometers, or even less than 70, less than 50 nanometers, less than 20 nanometers, less than 10 nanometers, or less than 5 nanometers. In some embodiments, the cross-sectional dimension can be less than 2 nanometers or 1 nanometer.

In some embodiments, the nanostructure has at least one cross-sectional dimension ranging from 0.5 nanometers to 200 nanometers, or from 1 nm to 100 nm, or from 1 nm to 50 nm.

The length of a nano structure expresses its elongation extent generally perpendicularly to its cross-section. According to some embodiments of the present invention the length of the nanostructure ranges from 10 nm to 50 microns.

The cross-section of the elongated nanostructure may have any arbitrary shape, including, but not limited to, circular, square, rectangular, elliptical and tubular. Regular and irregular shapes are included.

In various exemplary embodiments of the invention the nanostructure is a non-hollow structure, referred to herein as "nanowire".

A "wire" refers to any material having conductivity, namely having an ability to pass charge through itself.

In experiments performed according to some embodiments of the present invention silicon nanowires, about 20 nm in diameter and about 10 μm in length, have been employed.

In some embodiments, a nanowire has an average diameter that ranges from 0.5 nanometers to 200 nanometers, or from 1 nm to 100 nm, or from 1 nm to 50 nm.

In some embodiments of the present invention, the nanostructure is shaped as hollow tubes, preferably entirely hollow along their longitudinal axis, referred to herein as "nanotube" or as "nanotubular structure".

The nanotubes can be single-walled nanotubes, multi-walled nanotubes or a combination thereof.

In some embodiments, an average inner diameter of a nanotube ranges from 0.5 nanometers to 200 nanometers, or from 1 nm to 100 nm, or from 1 nm to 50 nm.

In case of multi-walled nanotubes, in some embodiments, an interwall distance can range from 0.5 nanometers to 200 nanometers, or from 1 nm to 100 nm, or from 1 nm to 50 nm.

It is appreciated that while FIG. 8A shows a single nanostructure 40, some embodiments contemplate a configuration in which sensor 20 comprises a plurality (i.e., two or more) of nanostructure. When a plurality of nanostructures is employed, the nanostructures 40 are optionally and preferably arranged in an array. For example, the nanostructures can be arranged generally parallel to each other, as schematically illustrated in FIG. 8B.

Selection of suitable materials for forming nanostructure 40 as described herein will be apparent and readily reproducible by those of ordinary skill in the art, in view of the guidelines provided herein for beneficially practicing embodiments of the invention. For example, nanostructure 40 of the present embodiments can be made of an elemental semiconductor of Group IV, and various combinations of two or more elements from any of Groups II, III, IV, V and VI of the periodic table of the elements.

As used herein, the term "Group" is given its usual definition as understood by one of ordinary skill in the art. For instance, Group III elements include B, Al, Ga, In and Tl; Group IV elements include C, Si, Ge, Sn and Pb; Group V elements include N, P, As, Sb and Bi; and Group VI elements include O, S, Se, Te and Po.

In some embodiments of the present invention the nanostructure is made of a semiconductor material, optionally and preferably a semiconductor material that is doped with donor atoms, known as "dopant". The present embodiments contemplate doping to effect both n-type (an excess of electrons than what completes a lattice structure lattice structure) and p-type (a deficit of electrons than what completes a lattice structure) doping. The extra electrons in the n-type material or the holes (deficit of electrons) left in the p-type material serve as negative and positive charge carriers, respectively. Donor atoms suitable as p-type dopants and as n-type dopants are known in the art.

For example, the nanostructure can be made from silicon doped with, e.g., B (typically, but not necessarily Diborane), Ga or Al, to provide a p-type semiconductor nanostructure, or with P (typically, but not necessarily Phosphine), As or Sb or to provide an n-type semiconductor nanostructure.

In experiments performed by the present inventors, Si nanowires and p-type Si nanowires with a diborane dopant have been utilized.

In some embodiments of the present invention the nanostructure is made of, or comprises, a conductive material, e.g., carbon. For example, the nanostructure can be a carbon nanotube, either single-walled nanotubes (SWNT), which are can be considered as long wrapped graphene sheets, or multi walled nanotubes (MWNT) which can be considered as a collection of concentric SWNTs with different diameters. A typical diameter of a SWNT is less of the order of a few nanometers and a typical diameter of a MWNT is of the order of a few tens to several hundreds of nanometers.

When a plurality of nano structures is employed, the nanostructures can be grown using, for example, chemical vapor deposition. Alternatively, the nanostructures can be made using laser assisted catalytic growth (LCG). Any method for forming a semiconductor nanostructure and of constructing an array of a plurality of nanostructures is contemplated. When a plurality of nanostructures 40 is employed, there is an affinity moiety 48 immobilized on each of the nanostructures. In some embodiments of the present invention all the affinity moieties are the same across all the nanostructures, and in some embodiments at least two nanostructures are attached to different affinity moieties.

A reaction event between marker or biomarker 50 and moiety 48 changes the surface potential of nanostructure 40 and therefore results in a change of an electrical property of nanostructure 40. For example, nanostructure 40 can exhibit a change in density of electrons or holes over some region of nanostructure 40 or over the entire length of nanostructure 40. Nanostructure 40 can additionally or alternatively exhibit a change in its conductivity or resistivity.

Referring again to FIG. 7, the method optionally and preferably proceeds to 12 at which the liquid or biological liquid is washed off the sensor, and to 13 at which the presence and/or concentration of the marker or biomarker is detected based on a detectable signal received from the sensor within a time-window beginning a predetermined time period (e.g., at least 10 seconds or at least 20 seconds or at least 30 seconds or at least 45 seconds or at least 60 seconds or at least 75 seconds or at least 90 seconds or at least 105 seconds or at least 120 seconds or at least 135 seconds or at least 150 seconds) after the beginning time of the washing 12. Preferably, the detection is based on signal received within the time-window, but is not based on signal received from the sensor before the beginning time of the time-window. The duration of the time-window is preferably from about 30 seconds to about 500 seconds. Other predetermined time periods and time-window durations, including predetermined time periods and time-window durations that are outside the above ranges, are also contemplated.

According to some embodiments of the invention the signal is monitored from the beginning of the washing, more preferably from immediately before or immediately after the initiation of the washing, but the beginning of the time-window during which the signals on which the determination of the presence or level of the marker is based, is not at the beginning of the washing. In these embodiments, the method optionally and preferably determines the beginning of the time-window from the signal itself. This can be done, for example, by monitoring the time-dependence of the signal (e.g., slope, plateau, zeroing of some derivative with respect to the time, value of some derivative with respect to the time, etc.), and identifying the beginning of the time-window based on a change in the time-dependence. For example, the method can identify the beginning of the time-window as a time point at which the signal exhibits a decrement, or a time point at which the signal exits a plateau region.

The detection is optionally and preferably by monitoring the change in the electrical property of nanostructure 40 using an arrangement of electrodes. With reference to FIGS. 8A and 8B, in some embodiments of the present invention sensor 20 comprises a source electrode 42 and a drain electrode 44, wherein nanostructure 40 is disposed between electrodes 42 and 44 and serves as a charge carrier channel. Optionally, sensor 20 also comprises a gate electrode 46, forming, together with electrodes 42 and 44 and nanostructure 40, a transistor, e.g., a field effect transistor (FET). The gate electrode 46 is optionally and preferably, but not necessarily, spaced apart from nanostructure 40 by a gap 47. A gate voltage can be applied to channel nanostructure 40 through gate electrode 46. In some embodiments, when the voltage of gate electrode 46 is zero, nanostructure 40 does not contain any free charge carriers and is essentially an insulator. As the gate voltage is increased, the electric field caused attracts electrons (or more generally, charge carriers) from source electrode 42 and drain electrode 44, and nanostructure 40 becomes conducting. In some embodiments, no gate voltage is applied and the change in the charge carrier density is effected solely by virtue of the interaction between affinity moiety 48 and marker or biomarker 50.

The electrodes of sensor 20 can be connected directly or indirectly to a circuit (not shown). The circuit can apply voltage to nanostructure 40 via one or more of the electrodes, and monitors the changes in the electrical property of nanostructure 40 responsively to the binding of marker or biomarker 50 to affinity moiety 48. The circuit can be constructed, for example, for measuring an electrical measure corresponding to a change in the electrical property of nanostructure(s) 40. The electrical measure can be, e.g., voltage, current, conductivity, resistance, impedance, inductance, charge, etc.

The method optionally and preferably continues to 14 at which the liquid or biological liquid is contacted with another sensor, which is preferably non-specific to the marker or biomarker 50. In these embodiments, the method optionally and preferably continues to 15 at which the liquid or biological liquid is washed also off the non-specific sensor. When operations 14 and 15 are executed, the detection of the presence and/or concentration of the marker or biomarker is optionally and preferably based on a comparison 16 between the detectable signal and a background signal received from the non-specific sensor. A detection based on the comparison is generally shown at 17.

The method ends at 18.

FIG. 9 is a schematic illustration of a system 90 for detecting a presence and/or concentration of a marker or biomarker 50 (not shown) in a liquid or biological liquid 92, according to some embodiments of the present invention.

System 90 can be used for executing one or more, more preferably all, the operations of method 10. System 90 can comprise a fluidic device 94 having a sensing chamber 96 and a sensor, such as, but not limited to, sensor 20, in the sensing chamber 96. System 90 can optionally and preferably comprise a flow control system 98 for introducing a washing buffer 100 to chamber 96 to wash liquid or biological liquid 92 off sensor 20, and a signal analyzer 102 having a circuit 104 for analyzing detectable signals received from sensor 20, as further detailed hereinabove.

In some embodiments of the present invention fluidic device 94 comprises a non-specific sensor 106, which is non-specific the marker or biomarker, as further detailed hereinabove. Sensor 106 can be in the same sensing chamber 96 as sensor 20. In these embodiments, the circuit 102 of signal analyzer 104 can compare between the detectable signal and the background signal, and detect the presence and/or concentration of the marker or biomarker based on the comparison, as further detailed hereinabove.

As used herein the term "about" refers to ±10% or ±5%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

The following presents some of advantages of the methodology of the present embodiments over other technologies:

Sensitivity from femtoMolar to nanoMolar range (biomarker concentration in the sample);
Fast results, after less than about 5 minutes;
Real-time ultra-sensitive monitoring;
Rapid and lack of time consuming processes (i.e. centrifugation, dialysis, affinity columns);
Label-free: less steps to worry about, do not need to excite and image;
Multiplex: extract as much biological data as possible;
Overcoming the Debye screening length;
Easy to integrate with a lab on chip system;
Work with very small volume sample;
Reusable/reversible;
Low-cost.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Example 1

Fabrication of SiNW-FET

FIGS. 1A-G are images (FIGS. 1A and 1B) and schematic illustrations of a fabrication process (FIGS. 1C-G) of a 20 nm diameter P-type SiNW-FET device on 3 inch silicon wafer with 600 nm oxide layer, according to some embodiments of the present invention.

Figure 1A:
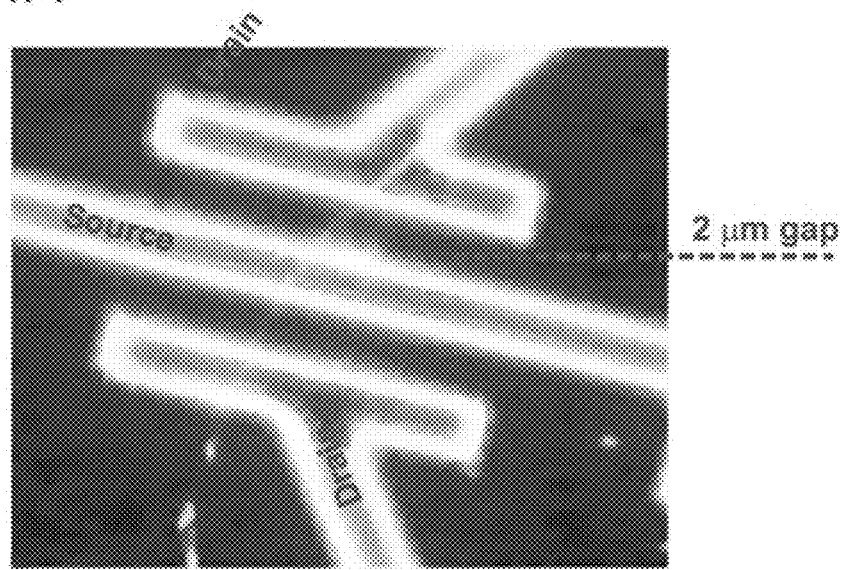
Figure 1B:
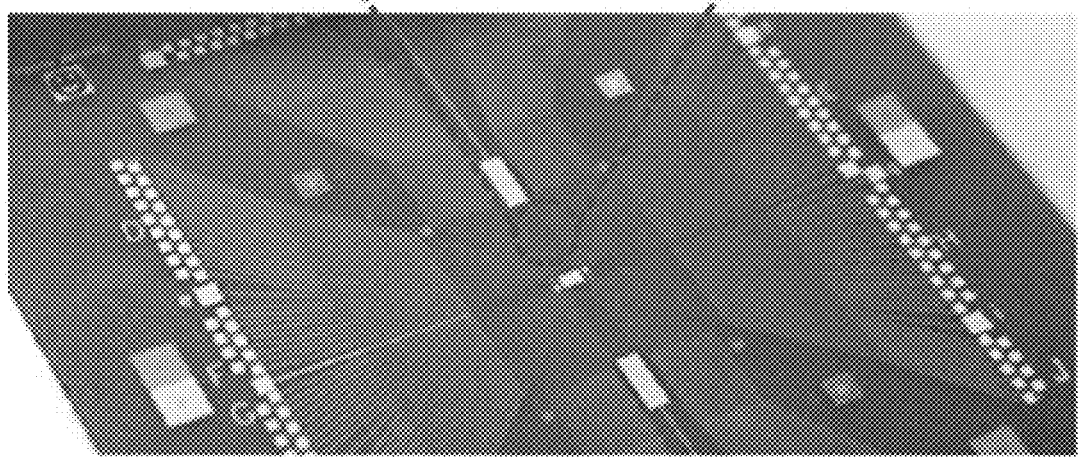

P-type SiNWs were synthesized by chemical vapor deposition (CVD) system (via vapor liquid solid (VLS) process) (FIG. 1C). The p-type SiNWs were deposited on silicon substrate with 600 nm oxide layer and outer metal pads (5 nm Cr and then 60 nm Au), that were fabricated in advance by lithography (FIG. 1D). Source and drain electrodes were deposited with the use of a multilayer photoresist structure consisting of 500 nm LOR5A (Microchem) and 500 nm 1805 (Shipley). After exposure and development of the electrode patterns (FIG. 1E), the contacts were metallized by e-beam and thermal evaporation of Ni (60 nm) respectively, and were then passivated with an insulating layer of $Si_3N_4$ (60 nm thick) deposited by plasma-enhanced chemical vapor deposition at 80° C. (ICP-PECVD, Axic Inc.) and a layer of 10 nm alumina (ALD deposition using a Cambridge Nanotech Savannah 200 system) (FIG. 1F). A lift-off of unexposed photoresists layers and a thermal annealing of SiNWs and metal contacts were preformed (FIG. 1G). The separation between the source and drain electrodes for each FET was about 2 μm. An image and a magnified image of the FET are shown in FIGS. 1B and 1A, respectively.

Example 2

Preparation of SiNW Modified with Antibodies

A modification of silicon nanowires (SiNW) FET device with antibodies is schematically illustrated in FIG. 2. The process is briefly described as follows:

Surface Cleaning and Activation:

a SiNW FET prepared as described in Example 1 herein was washed with acetone, deionized water and isopropanol; Dried under $N_2$ stream; and the surface was thereafter activated for silanization with oxygen plasma (0.200 torr, 100 W, 10 minutes).

Silanization:

The device surface was covered with (3-aminopropyl)-dimethyl-ethoxysilane and heated to 50° C. for 60 minutes. Thereafter the surface was washed with isopropanol, followed by dehydration on hot plate (115° C., 30 minutes).

Cross Linker Binding:

The device with was covered with 8.3% glutaraldehyde containing 12 mM sodium cyanoborohydride in phosphate buffer 10 mM, pH=8.5 (60 minutes, room temperature). Thereafter, the device was washed with deionized water, acetone, isopropanol and deionized water again.

Channel Assembly on the Chip:

The tubing and PDMS channel were washed with isopropanol and deionized water. The tubing was thereafter connected to a syringe pump, and the system was washed by introducing phosphate buffer (PB) (10 mM, pH=8.5).

Antibody Immobilization:

CA 15-3 igG (40 μl, 1 mg/ml) was mixed gently with 700 μl phosphate buffer (10 mM, pH=8.5) containing 12 mM sodium cyanoborohydride. The Antibody solution was introduced into the system (at 4° C., overnight about 16 hours), and the tubing system was thereafter washed with phosphate buffer (10 mM, pH=8.5) while keeping the surface under the channel always wet.

Blocking:

A blocking solution containing ethanolamine (100 mM) and 12 mM sodium cyanoborohydride in PB (pH=8.5) was introduced into the system during 3 hours at room temperature, at a flow rate of 50 μl/minute. The system was thereafter washed with phosphate buffer (10 mM, pH=8.5) at a flow rate of 50 μl/minute, for 30 minutes. The as prepared system was used for sensing.

Example 3

Sensing

A fluidic system containing the a plurality of SiNW FET as described in Example 2 above, was studied experimentally, using an antigen-containing buffer, a washing buffer and a bio-sample. In this example, the SiNW FET was modified with anti-troponin T (Fab2 fragment).

The antigen-containing buffer included the antigen cardiac troponin T, 10 nM. The washing buffer included 150 μM phosphate buffer.

FIG. 3 presents an exemplary response calibration curve the antibody-modified SiNW FET, upon introducing of an antigen-containing buffer, following by introducing a washing buffer into a fluidic system containing the a plurality of SiNW FET.

The arrow A in FIG. 3 denotes the time point at which the antigen-containing buffer was introduced into the fluidic system. At this point, the antigen was absorbed on the SiNW surfaces due to interactions with the antibody, and a change in the electric response is detected. The arrow B in FIG. 3 denotes the time point at which the washing buffer was introduced into the fluidic system. At this point, most of the bound antigen was desorbed from the SiNWs, and a reverse change in electric response is detected. The parameters used for the FET are Vg=0 volt, Vds=0.1 volt. The flow rate in the fluidic system was 20 μl/min, generated by Mitos pump.

FIG. 4 presents calibrated response of antibody-modified SiNW FET, in a bio-sample. In this experiment, the bio-sample was fetal bovine serum. The arrow A in FIG. 4, denotes the time point at which the bio-sample was introduced into the system. The parameters used for the FET are Vg=0 volts, Vds=0.2 volts. The flow rate in the fluidic system was 100 μl/min.

FIG. 5 presents a response calibration curve in the presence of the bio-sample of FIG. 4, but after initiation of a washing operation. The arrow B in FIG. 5, denotes the time point at which the washing buffer was introduced into the system. The parameters used for the FET and the flow rate were the same as in FIG. 4 above. A concentration of less than 30 units/ml CA 15-3 produces a detectable change in electric response.

FIG. 6 shows two response calibration curves obtainable in the presence of a bio-sample, after the initiation of a washing operation. The arrow B in FIG. 6 denotes the time point at which the washing buffer was introduced into the system. A first response calibration curve corresponds to the desorption of the biomarker from a sensor with affinity moiety, and the second calibration curve corresponds to the desorption of the biomarker from a sensor without affinity moiety. The second calibration curve can be defined as the background to which the first curve can be compared.

Example 4

Detailed Study

This example demonstrate the application of antigen-dissociation regime, from antibody-modified Si-nanowire sensors, as a simple and effective direct sensing mechanism of biomarkers of interest in complex biosamples, such as serum and untreated blood, which does not require ex situ time-consuming biosample manipulation steps, such as centrifugation, filtering, preconcentration, and desalting, thus overcoming the detrimental Debye screening limitation of nanowire-based biosensors.

A fluid-delivery device was fabricated from flexible polydimethylsiloxane (PDMS) elastomer. The PDMS was incubated with curing agent at 10:1 mass ratio for overnight at 60° C. The resulting device was then cut into rectangular pieces, at dimensions of 10×10×5 mm. Two channels of different dimensions were used in this study: a rectangular chamber of larger dimensions (h=5 mm, l=7 mm and w=3 mm), and a rectangular smaller chamber (h=0.1 mm, l=3.5 mm and w=1 mm). An upstream polyethylene tube (PE 20, Intramedic) was 14 cm long and had 0.38 mm inner diameter. A downstream Tygon tube (S-50-HL, Tygon) was 13 cm long.

A chip with an array of SiNW FET were chemically-modified to perform sensing of binding and unbinding kinetics of antigen by immobilized antibody on the SiNW FET surface. In order to conjugate the antibody to the SiNWs surface, the chip was first washed with acetone (9005-68, J. T. Baker), isopropanol (9079-05, J. T. Baker), and deionized water (18 MΩ·cm) successively, followed by nitrogen drying. Then, oxygen plasma (100 W, 0.2 Torr) was applied for 10 minutes. The chip was covered by glass dish and inserted to glove box (150B-G, Mbraun) under argon atmosphere (water and oxygen free) to apply the aminosilane modification. Immediately afterwards, the chip was covered with about 150 µl (3-aminopropyl)-dimethyl-ethoxysilane (APDMES; SIA0603.0, Gelest) for 60 minutes. Then, the chip was washed three times with about 30 ml of anhydrous toluene (99.8%, 244511, Sigma-Aldrich). The chip was transferred from the glove box to the clean room, and washed again with isopropanol followed by nitrogen drying. Next, the chip was placed on a hot plate at 115° C. for 30 minutes. The subsequent cross-linker binding was performed by covering the device with 8.3% glutaraldehyde solution, containing 12 mM sodium cyanoborohydride in 10 mM phosphate buffer, pH=8.5, for 60 minutes at room temperature, followed by subsequent washes with deionized water, acetone, isopropanol and deionized water.

PDMS channels that were pre-washed with isopropanol and deionized water, were then assembled to the chip by connecting the tubing to the syringe pump, followed by withdrawing 10 mM phosphate buffer, pH=8.5. The antibody was immobilized to the SiNW surface by withdrawing the antibody solution, containing 10-100 µg/ml IgG antibody, 12 mM sodium cyanoborohydride and 10 mM phosphate buffer, pH=8.5, into the system at 4° C. for overnight (about 16 hours). Blocking was performed by withdrawing the blocking solution, containing 100 mM ethanolamine and 12 mM sodium cyanoborohydride in 10 mM phosphate buffer, pH=8.5, into the system at a flow rate of 50 µl/min for 150 minutes at room temperature, followed by final wash with 10 mM phosphate buffer, pH=8.5, at a flow rate of 50 µl/min for 30.

The devices were wire-bonded (using wire-bonder, model 8850, West Bond) and the sensor device chip was integrated with the custom-made PDMS microfluidic channel. A data acquisition system was used to measure the current of the SiNW FETs (Ids), induced by surface charges alterations. The selected devices were examined for their performance in sensing buffer. Gate voltage sweep was used for transconductance measurements, and the subsequent determination of the transistor regime of operation. A suitable gate voltage was further selected to perform all the following sensing experiments. Sensing experiments were performed by monitoring the conductance of the SiNW devices over time (current-versus-time signals were recorded at 1 second intervals), during introduction of the analytes to the sensing chip by a syringe pump (Fusion 200, Chemyx) via the microfluidic system.

FIGS. 22A and 22B show electrical characterization of p-type SiNW FET nanodevices under water-gate configuration. FIG. 22A is a plot of source-drain current versus source-drain voltage (Vsd) at different gate voltages (Vg). FIG. 22B is a plot of source-drain current versus gate voltages (Vg) at 0.1 V source-drain voltage (Vg).

FIGS. 23A and 23B are Scanning Electron Microscope (SEM) images of the SiNWs. FIG. 23A is SEM image of the synthesized 20 nm p-type SiNW via chemical vapor deposition system on silicon (100) wafer, and FIG. 23B is a SEM image of SiNW FET device consisting of SiNWs connected to source and drain electrodes.

It was found that the parameters that control the capability to perform quantitative biomarkers analysis in biosamples include (i) the affinity strength ($k_{off}$ rate) of the antibody-antigen recognition pair, which dictates the time length of the high-affinity slow dissociation sub-regime, and (ii) the flow rate applied during the solution exchange dissociation step, which controls the time width of the low-affinity fast dissociation sub-regime. The lack of ex situ biosample manipulation time-consuming processes enhances the portability of the sensing platform and reduces to minimum the required volume of tested sample, as it allows the direct detection of untreated biosamples (5-10 µL blood or serum), while readily reducing the detection cycle duration to less than 5 min, factors of great importance in near-future point-of-care medical applications.

Analysis of the dissociation regime of an antigen from its specific antibody-modified SiNW FET device is demonstrated as an effective and straightforward approach for the sensitive, selective, and direct detection of biomarkers from complex biosamples.

The biosample containing the analyte biomarker was introduced to the SiNW FET sensing nanodevice. The surface of the SiNW modified with the antibody specifically interacted with the analyte biomarker. As a result of antibody-antigen interaction, the biomarker molecules strongly and selectively bind to the antibody units attached to the surface of the nanowire FET device. In physiological solutions such as serum or blood, it may be difficult to discern the specific binding of the biomarker analyte cannot be directly from the background signal change, due to the charge screening caused by the high concentration of charged chemical species, such as salts and proteins.

After the selective association of the biomarker molecules, the device is rapidly flushed out with a controlled solution of low ionic strength, the sensing buffer, wherein the SiNW FET device can effectively sense the change in the surface charge on the nanowire, due to the strongly bound antigen species, without the masking effects of unbound nonspecific chemical species. Rapid washing of the sensing devices with the sensing buffer results in the fast removal of unbound, or loosely bound, nonspecific chemical species (salts, proteins, cells, small molecules) from the nanowire surface proximity, leaving behind only specific antigen molecules attached via strong and specific interactions to the nanowire surface, revealing considerably slower dissociation kinetics.

This effect efficiently splits the "dissociation regime window" into two sub-regimes: (i) At the beginning, when the low ionic strength "sensing buffer" is flushed through to the SiNWs FET sensing array, the low-affinity entities (salts, biomolecules, proteins, etc.) speedily leave the SiNWs surface, which results in a rapid change in the conductivity of the devices. (ii) After the removal of the low affinity entities ends (the unspecific dissociation sub-regime), the specific dissociation of high-affinity entities (the specific desorption sub-regime) dominates the change of the conductivity of the device. The point of transition between the unspecific and specific dissociation sub-regimes is finally applied for the sensitive and accurate detection of biomarker proteins.

This approach represents the direct analysis of complex biosamples on a single platform, able to selectively detect low-concentration specific biomarkers, while easily removing unwanted chemical species (salts, biomolecules, proteins, cells), without the requirement for time-consuming steps such as centrifugation, desalting, or affinity columns. The whole ultrasensitive protein label-free analysis process can be practically performed quickly, for example, in less than 5 min.

FIG. 10 schematically describes the operation principle of the dissociation regime detection approach of an antigen from antibody-modified SiNW FET sensing devices, according to some embodiments of the present invention. Initially, the immobilized SiNW device is introduced to low ionic strength sensing buffer aiming to achieve a stable baseline. Next, a biosample is introduced either to a SiNW FET device that is modified with a specific antibody, or to a SiNW FET device that is modified with nonimmuno active protein, FIG. 10, section (1).

The interaction of the SiNW FET device with biomolecules in the analyzed sample alters the conductivity of the device during the binding regime window, FIG. 10, section (2). At this point, the SiNW FET device cannot distinguish between the change in the conductivity that is caused by the binding of the specific antigen or by other biomolecules and salts in the sample, due to charge screening effects in high ionic strength solutions. When the SiNW FET device is introduced back to low ionic strength sensing buffer, through rapid flush out of the sensing chamber, the unbound biomolecules and salts from the biosample are removed from the surface of the SiNW FET device in a manner that depends upon the strength of the interaction between them.

In the case of SiNW FET devices modified with an antibody, the presence of the specific antigen will reduce the rate of returning to baseline, due to the much slower desorption kinetics of the antigen from its specific antibody, FIG. 10, section (3). However, when the SiNW surface is modified with a nonspecific antibody, or when there is no antigen in the sample, the rate of returning to baseline is considerably faster, due to the absence of specific high-affinity interactions.

FIG. 11 shows normalized association response of a representative anti-CA 15-3 immobilized SiNW FET sensing device against various concentrations of the target antigen CA 15-3 in unprocessed serum samples. The black curve represents the response of the FET device to CA 15-3-free fetal bovine serum control sample. The red, blue, and turquoise curves represent the responses of the FET sensing device to samples containing CA 15-3 antigen concentrations of 55, 135, and 535 pM in unprocessed fetal bovine serum, respectively. The black arrow depicts the sensing device electrical baseline under the flow of low ionic-strength sensing buffer (sensing buffer-SB, 155 µM sodium phosphate buffer pH abut 8.0) through the microfluidic channel before the injection of biosamples. The blue arrow indicates the time of injection of the unprocessed serum biosamples (high ionic-strength samples). Non-analytical sensing information can be extracted from the association curves under these conditions. The Inset of FIG. 11 shows raw data curves of the interaction of the same sensing device against biosamples containing different concentrations of the CA 15-3 target antigen.

The Debye length limitation predicts that the nano-FET device will not be able to sense the antigen-antibody high-affinity interactions under high ionic strength physiological conditions (Debye length is approximately 1 nm). Thus, the measured antigen association curves cannot be translated to analytical signals (see FIG. 11). The association curves obtained in serum samples demonstrate high similarity between the normalized electrical responses of the monoclonal antibody-modified nanowire device against various concentrations of the CA 15-3 antigen (human-cancer associated antigen), from 0 to 535 pM, which is a biomarker for breast cancer diagnosis and monitoring. No analytical differences are observed for the interaction of the SiNW FET sensing devices against different concentrations of the tested CA 15-3 antigen in unprocessed serum samples, due to the high ionic strength of the biosample, thus preventing the use of the association-regime curves as an analytical means for the real time detection of biomolecular species. These results, therefore, demonstrate the strong requirement for the development of novel nano-FET-based detection approaches for the direct detection of protein biomarkers in untreated biosample solutions, e.g., blood.

FIG. 12 shows normalized electrical response of a representative antitroponin antibody-modified SiNW FET sensing device to the association and dissociation of its specific antigen troponin T (cTnT, 1 nM) under low-ionic strength conditions (sensing buffer, SB, 155 µM sodium phosphate buffer pH of about 8.0) (red curve). Also shown (Black curve) is a normalized electrical response of a representative antitroponin antibody-modified SiNW FET sensing device against a BSA containing sample (bovine serum albumin, 1 nM) under low ionic strength conditions (sensing buffer, SB, 155 µM sodium phosphate buffer pH of about 8.0). The black arrow depicts the sensing device electrical baseline under the flow of low ionic-strength sensing buffer (sensing buffer-SB, 155 µM sodium phosphate buffer pH of about 8.0) through the microfluidic channel before the injection of the corresponding samples. The blue arrow indicates the time of introduction of either cardiac troponin T (the antigen, marked by a red line) or bovine serum albumin (the serum protein, marked by a black line) samples to the SiNW FET devices (association step). The green arrow indicates the subsequent washing step with sensing buffer (dissociation step).

In the specific case demonstrated in this example, cardiac troponin T, a very important marker of heart failure, was used as an antigen, while the antigen-binding monoclonal antibody against cardiac troponin T (cTnT) was used as the specific antibody receptor immobilized to the SiNW FETs surface. Initially, the SiNW FET devices are exposed to sensing buffer solution, SB, and the devices' electrical responses are normalized according to EQ. 1, below $$100\% \times (I_{SB} - I_t)/I_{SB}. \quad \text{(EQ. 1)}$$

where $I_{SB}$ is the current in sensing buffer (SB) and It is the current at a certain time point during the measurement.

Next, a sample containing cardiac troponin T antigen in sensing buffer was introduced into the detection channel (indicated in FIG. 12 by blue arrow), leading to a sharp increase in the concentration of free troponin molecules in the close vicinity of the nanodevices' surface, followed by the gradual high-affinity association of troponin molecules to the surface-immobilized antibody units. As a result, the normalized electrical response of the devices increases, until reaching a saturation point or plateau, indicating the maximum amount of bound troponin antigen to the nanodevices' surface. Next, the sensing nanodevices were rapidly flushed with the low ionic-strength sensing buffer. The amount of bound troponin molecules gradually decreased in response, until reaching the original sensing buffer baseline electrical signal. Noteworthy, the observed dissociation kinetics of troponin antigen is considerably slower than its association kinetics. These observations are consistent with the expected high-affinity interactions between the immobilized antibody receptor units and the antigen molecules.

When exposing the SiNW FET devices, modified with anti-cTnT antibody receptor units, to a low ionic strength solution containing a high concentration of the protein BSA (bovine serum albumin), no significant change in the conductivity of the respective devices was observed. These findings demonstrate that the association of protein molecules to the antibody-modified SiNW-based sensing devices is dominated by specific high affinity antigen-antibody interactions, and that the surface chemistry on the nanowires prevents the nonspecific binding of biomolecules other than the specific target antigen molecules. The antigen association curves obtained under low-ionic strength conditions allow extracting the saturation time where the association of the antigen molecules reaches a plateau. All further dissociation experimental data was achieved after antigen association reaches a plateau, for consistency purposes.

By performing a rapid flush-out step of the antibody-modified SiNW devices using a low ionic strength sensing buffer, after complete association of the specific antigen molecules has been reached, the device is capable to analytically split the dissociation regime time window into two discrete dissociation sub-regimes: (i) a fast-dissociation kinetics sub-regime related to low-affinity interacting chemical entities (e.g., salts, nonspecific proteins, cells, and small chemical species), and (ii) a slow-dissociation kinetics sub-regime related to high-affinity interacting chemical entities (e.g., the specific antigens).

In other words, the flushing operation using the low ionic strength sensing buffer allows for the simultaneous fast removal of low-affinity fast-dissociating unbound, or loosely bound, nonspecific molecules from the close vicinity of the nanowires surface, thus minimizing the charge screening effects caused by these charged species, accompanied by the resulting capability to measure the presence of high-affinity slow dissociating bound antigen species, after the complete removal of low-affinity species is achieved. A considerably contrasting dissociating kinetics rate for the fast-dissociating species, in comparison with the dissociation rates of the slow dissociating species, $k_{off}^{antigen} \gg k_{off}^{nonspecific}$ species, allows to experimentally split the dissociation window regime into the above-mentioned sub-regimes. Thus, both the intrinsic affinity constant of the selected surface-attached antibody, as well as the applied flow rate during the SB flushing step can be selected to perform accurate quantitative detection of the antigen species based on the dissociation regime window.

In various exemplary embodiments of the invention the rapid ionic strength exchange step using the SB solution does not affect significantly the amount of specifically bound antigen species. This can be ensured, for example, by selecting the time window such that the antigen-antibody pair dissociation time is considerably longer than the time-window for complete removal of unbound, and weakly bound, nonspecific species (the nonspecific dissociation sub-regime). The nonspecific species dissociation time window can be controlled and shortened by increasing the flow rate of the flushing SB solution during the dissociation regime window.

The antigen dissociation regime window was tested as a potential means for the quantitative detection of biomarkers in complex biosamples, for two model antibody systems characterized by highly dissimilar affinity/dissociation constants. First, an anti-troponin antibody fragment, which represents a structurally modified fragment of the whole wild-type antibody molecule with a lower association affinity against the antigen than the original whole antibody, was employed aimed at testing our hypothesis. The results are shown in FIG. 13 which shows anti-troponin antibody dissociation curve in serum, together with a fit, under slow-flow conditions. The dissociation rate, off-rate $k_{off}$, for the antitroponing antibody fragment was extracted from the antigen dissociation curves measured under low ionic strength SB, and estimated to be $k_{off}=1.2\times10^{-2}$ s$^{-1}$.

FIGS. 14A and 14B show results of a comparison between the dissociation kinetics of the troponin T antigen-containing serum sample (at a troponin concentration of 10 nM) from the (F(ab')2)-immobilized SiNW FET devices and control troponin T-free serum sample. Measurements were conducted as follows. At first, the sample (either troponin T-containing serum or troponin T free serum control sample) was introduced to the immobilized SiNW FET devices through a microfluidic channel, at a flow rate of 100 μL/min (1 chamber volume exchange per minute, chamber volume 100 μL) until reaching the association plateau. Next, the immobilized SiNW FET devices are washed with the low ionic strength sensing buffer. The resulting dissociation kinetic curves demonstrate a similar temporal change of the normalized electrical response for both, the troponin T-containing serum sample and the troponin-free control sample (FIGS. 14A and 14B, red and black curves). The nanoFET devices show a relatively fast return to the baseline electrical response (under low ionic strength sensing buffer) and similar dissociation-related temporal electrical responses, implying the concurrent dissociation of nonspecific species together with the specific biomarker molecules, with an apparent $k_{off}$ of about $2.5\times10^{-2}$ s$^{-1}$ for the antigen-free serum sample. FIG. 15 shows the serum dissociation curve, together with a fit, under slow-flow conditions.

The low-affinity anti-troponin antibody receptor selected is thus less suitable for effective splitting of the dissociation regime window and the quantitative detection of the antigen molecules in the complex biosample.

Next, an antibody receptor with a significantly stronger binding affinity to its specific antigen was used. The use of a higher-affinity antibody, characterized by a lower dissociation rate from its antigen, leads longer dissociation times of the biomarker protein from the antibody-immobilized SiNW devices, hence enabling the separation of the low-affinity fast dissociation sub-regime (ionic species, nonspecific proteins, small chemicals, and cells) from the high-affinity slow dissociation sub-regime (the antigen). In the present example, a mouse monoclonal antihuman cancer antigen 15-3 IgG (Anti-CA 15-3), was used. FIG. 16 shows anti-CA 15-3 antibody dissociation curve in serum, together with a fit) under slow-flow conditions. The obtained $k_{off}$ was $k_{off}=6.2\times10^{-4}$ s$^{-1}$ indicating strong binding interaction against its antigen.

Figure 17A:
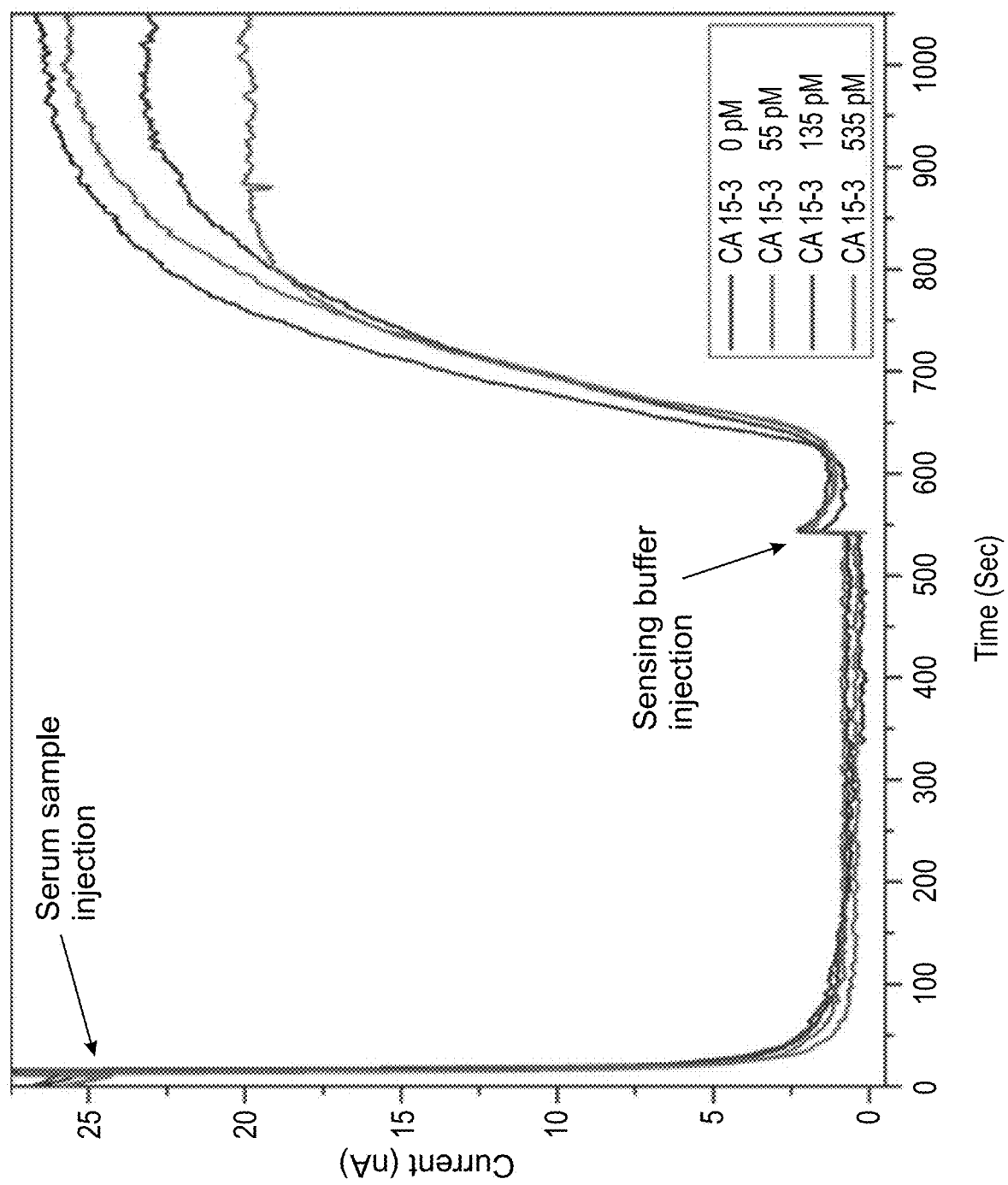
Figure 17B:
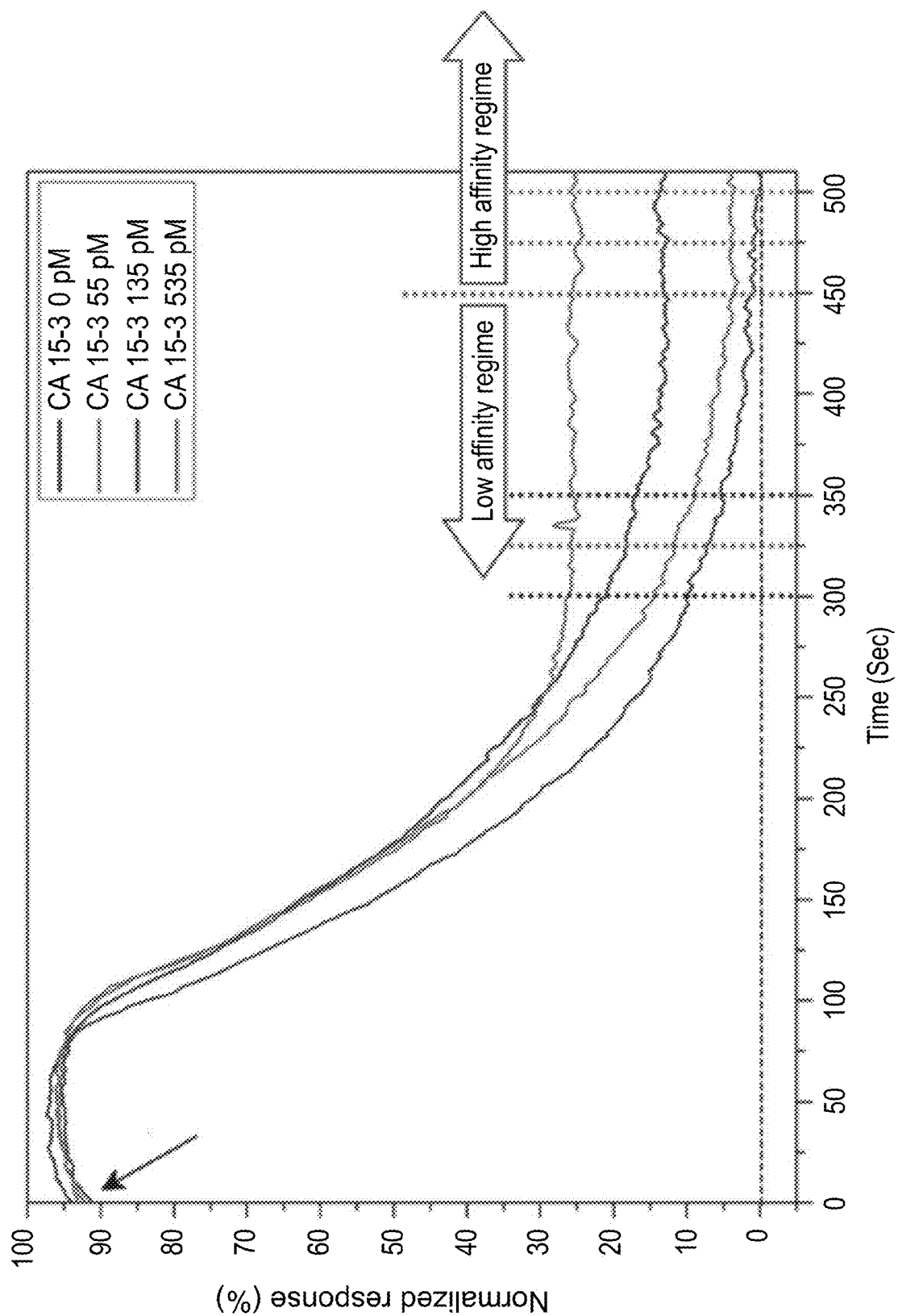
Figure 17C:
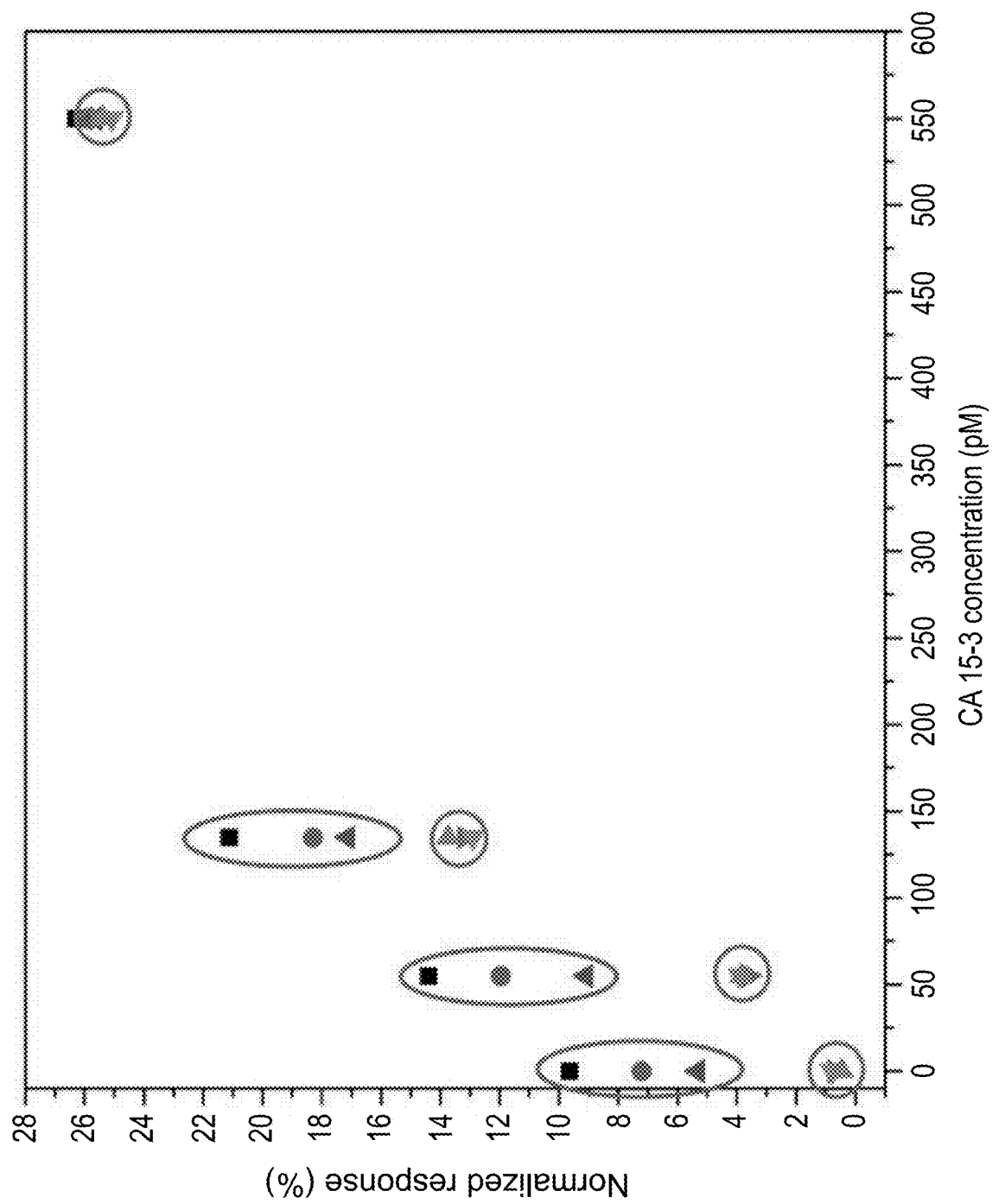
Figure 17D:
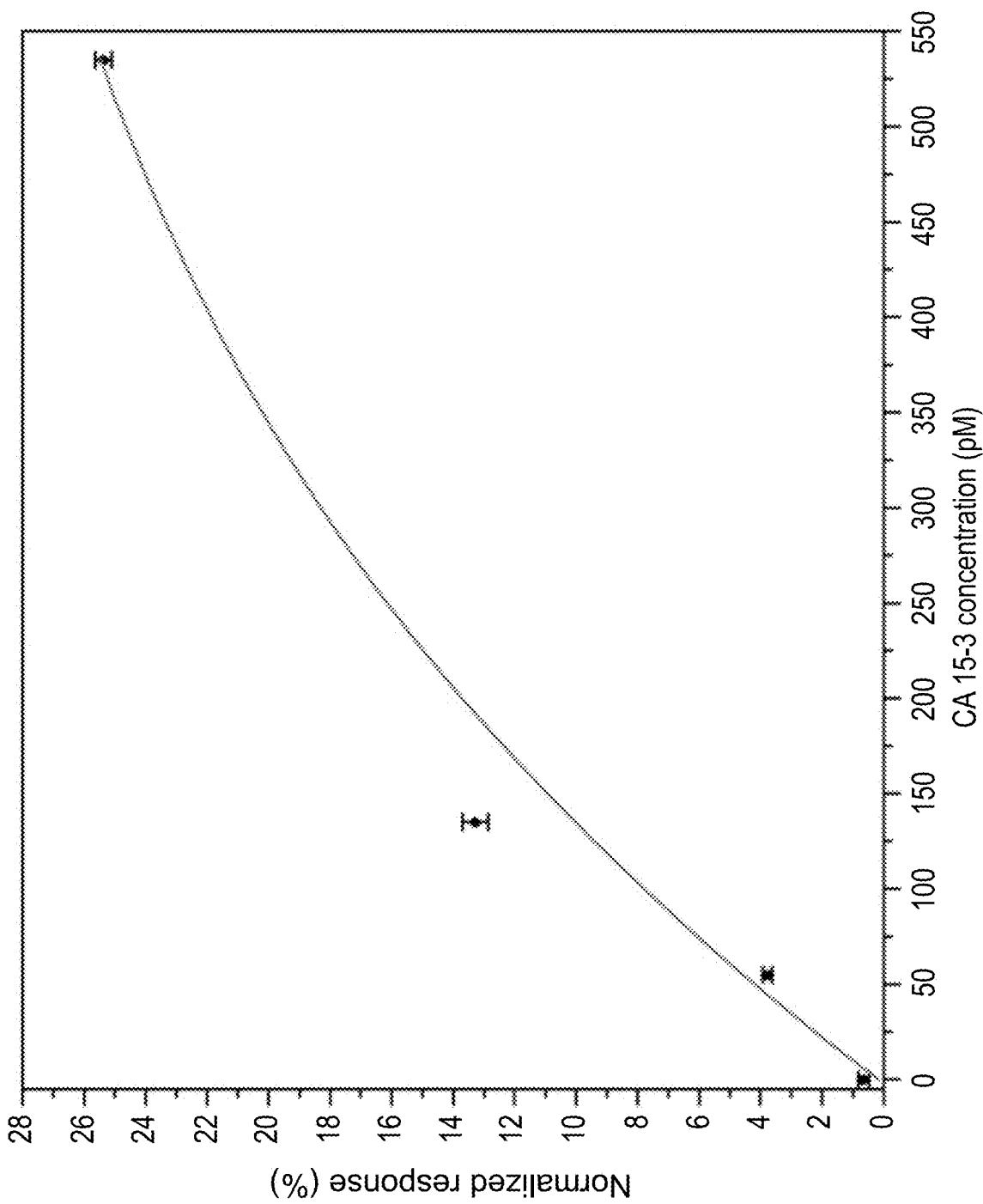

FIGS. 17A-D shows concentration-dependent sensing of the CA 15-3 antigen in unprocessed serum samples using the dissociation regime mode approach, at a low flow rate of 1 chamber-volume exchange per minute. In FIG. 17A, the black, red, blue, and turquoise curves show the complete raw electrical response of a representative anti-CA 15-3 modified SiNW FET sensing device to the association and dissociation (raising phase) of its specific antigen CA 15-3 in unprocessed bovine serum sample at concentrations of 0 (control antigen-free sample), 55, 135, and 535 pM, respectively. In FIG. 17B, the black, red, blue and turquoise curves show the normalized dissociation regime electrical response of the anti-CA 15-3-modified SiNW FET sensing device in unprocessed bovine serum sample at CA 15-3 concentrations of 0 (control antigen-free sample), 55, 135, and 535 pM, respectively. Each antigen sample was flowed for about 6 min (until reaching association plateau) before the washing-out with low-ionic strength sensing buffer was performed (sensing buffer-SB, 155 µM sodium phosphate buffer pH of about 8.0). The black arrow indicates the time of solution exchange from the unprocessed serum samples to the low-ionic strength sensing buffer. FIG. 17C shows concentration-dependent calibration curves of the CA 15-3 antigen extracted at different points of time along the measured dissociation regime curves in FIG. 17B. The black squares, red circles, and blue, green, pink and brown triangles correspond to points in time depicted as black, red, blue green, pink and brown dashed lines in FIG. 17B, respectively. The curves show that the analytically relevant high affinity regime, marked in turquoise circles, begins after 450 s along the dissociation curves in FIG. 17B. The red circles depict non-analytically relevant points in time along the dissociation regime curves. FIG. 17D shows concentration-dependent calibration plot of the CA 15-3 antigen, at the analytically relevant time points marked by turquoise circles in FIG. 17C).

FIGS. 17A-D demonstrate that the selection of a higher affinity antibody receptor allows for a deconvolution of the dissociation regime window into the two dissociation sub-regimes, an unspecific fast dissociation sub-regime and a specific slow dissociation sub-regime, with an inter-regime transition time of approximately 250 s at a flow rate of 100 µL/min (1 chamber volume exchange per minute, chamber volume 100 µL).

From the resulting curves (FIG. 17A), it is discernible that the dissociation window consists of two clearly separated sub-regimes, a fast dissociation zone lasting approximately 250 s, followed by a slow dissociation plateau-like zone that lasts for tens of minutes without a considerable change, and different in its amplitude from the electrical baseline signal of the devices prior interaction with the antigen under the low-ionic strength buffer. This observation demonstrates that the antigen molecules stay bound to the nanowire-immobilized antibody species for a period of time considerably longer than the time frame required for complete removal of the low-affinity nonspecific chemical species, $k_{off}^{antigen} > k_{off}^{nonspecific}$ species. This latter dissociation zone, characterized by an electrical response higher than the sensing buffer baseline electrical response (FIG. 17B, horizontal dashed blue line) displays a strong and reproducible dependence on the concentration of the antigen protein CA 15-3 in serum, which remains tightly bound to the SiNW FET device surface.

A further experimental evidence on the presence of the protein antigen confined to the surface of the nanodevices was demonstrated by the use of a regeneration buffer (glycine buffer, pH=3), which rapidly brings the dissociation of the high-affinity antigen-antibody pairs and causes the electrical response of the nanodevices to return to their initial baseline electrical level, after the subsequent flow of the low ionicstrength sensing solution. This is shown in FIG. 18, which is a graph of the regeneration curve of a CA 15-3 antigen from its antibody-modified nanowire device.

Additionally, concentration dependent experiments performed on untreated serum samples spiked with different concentrations of the CA 15-3 antigen reveal the robustness of this quantitative detection approach based on the simple examination of the dissociation regime window. As the concentration of CA 15-3 in the tested serum sample increases (FIG. 17B), more of the biomarker molecules associate to the SiNW devices surface, leading to stable larger electrical response (in relation to the SB baseline response).

The strong specific interaction between the anti-CA 15-3 and the antigen CA 15-3 allows the complete washing of the nonspecifically adsorbed salts and biomolecules within the sensing channel, performed by the fast flushing with low ionic strength sensing buffer, while maintaining the majority of surface-bounded CA 15-3 antigen molecules, in order to measure their sample concentration quantitatively.

Therefore, monitoring the dissociation regime of antigens from antibody-immobilized surfaces, with high-affinity capabilities, allows performing direct analytical detection using SiNW FET-based device, without applying any sample manipulation steps. This allows performing quantitative protein measurements, sensitive enough for the clinical diagnostics of CA 15-3 in relevant physiological concentration range (greater than 67 pM).

Thus, antibody species displaying dissociation rates in the range between $k_{off}$ of about $5\times10^{-3}$ s$^{-1}$ and about $1\times10^{-8}$ s$^{-1}$ can serve according to some embodiments of the present invention as detection receptors.

Through a controlled increase of the dissociation flow rate step, the nonspecific species dissociation sub-regime window can be selected such that antibodies of lower affinity may also be used.

In various exemplary embodiments of the invention complete association of the antigen species, for example, as verified by an electrical signal plateau, are achieved before the dissociation begins. This is advantageous when concentration dependent analytical sensing results is desired, since the final concentration of the antigen under test is calculated based on the difference between the baseline electrical signal under low ionic-strength conditions, prior to the antigen association, and the dissociation curve plateau achieved after complete removal of the low-affinity species from the vicinity of the sensing devices (high-affinity regime). Thus, changes in the amount of associated antigen species to the nanosensing devices, due to differences in the antigen-association time applied during the sensing may cause changes to the extracted concentration-dependent calibration curve.

Thus, in various exemplary embodiments of the invention a constant antigen association period of time, or, alternatively a complete association allowed, is applied for analytical consistency.

To quantitatively assess the antigen concentration, the transition time between the dissociation sub-regimes was firstly measured by exposing the sensing devices to an antigen-free serum sample. This sample served as reference for the extraction of the accurate time-point in which a complete removal of the low affinity species was achieved. After this point in time, an accurate quantitative assessment of the antigen concentration can be confidently performed, as demonstrated in FIGS. 17C and 17D, under the assumption of slow dissociation of the antigen species.

It was found by the inventors that such calibrating steps are not necessary. This will now be explained with reference to FIGS. 19A and 19B, which demonstrate multiplex single-chip differential detection of the CA 15-3 antigen by the use of specific and nonspecific chemically modified SiNWs FET devices, at a flow rate of 330 chamber-volumes per minute. Thus, the sensing arrays of the present embodiments can be fabricated with two main types of chemically modified nanodevices, wherein the first group represents the sensing nanodevices, chemically modified with the antibodies specific against the antigens under examination, and wherein the second group of nanodevices is chemically modified with a nonimmune reactive protein (or a nonspecific antibody receptor) and serves as on-chip internal reference devices.

The latter group of devices, due to the absence of specific interactions with the antigens in the biosample under test, only nonspecifically interact with low-affinity fast dissociating species present in the biosample, and allows simple extraction of the accurate transition time at which the first dissociation sub-regime is reached and a quantitative assessment of antigen concentration can be carried out. Thus, using these nonreactive on-chip reference devices allows for the simultaneous sensitive and quantitative detection of biomarkers in real time mode. In addition, increasing the flow rate of the dissociation-related flushing step can lead to a narrowing of the low affinity fast-dissociation sub-regime time window, and thus allow for a faster and more accurate quantitative detection of the antigen species. For this purpose a microfluidic chamber of smaller dimensions was used, so as to allow for considerably higher nominal flow rates (chamber volume exchange rate), using flow rates easily achievable with the fluidic pumping system.

Additionally, the use of smaller dimension microfluidic channels, instead of the previously used 100 µL larger chamber, can lead to a more efficient fluid exchange during the dissociation washing regime, along with the critical requirement of considerably lower biosample volumes, possibly lower than a few microliters. FIGS. 19A and 19B demonstrate the measurements performed aimed at the detection of the CA 13-5 biomarker based on the differential on-chip detection approach discussed above, this time using a considerably higher effective flow rate of 100 µL/min (chamber volume exchange rate is 330 chamber volumes per minute, chamber volume 0.3 µL).

By comparing the dissociation curves obtained from the nonimmune active protein-modified nanowire devices to the dissociation curves attained by the specific antibody-modified devices, the amount of the biomarker associated with the antibody-modified nanowire-based devices can be measured. The SiNW device modified with the protein BSA, which does not have specificity against the biomarker CA 15-3, reaches a plateau about 25 s after the flushing of the sensing buffer (FIG. 19A, red and blue curves). The antigen-free serum dissociation curve under fast-flow conditions is shown, together with a fit, in FIG. 20. The calculated $k_{off}$ was about $1.4 \times 10^{-1}$ s$^{-1}$.

The desorption kinetics from the antibody-modified SiNW device is considerably slower and correlates well with the concentration of the targeted antigen. The application of a faster solution exchange rate narrows the fast-dissociation sub-regime window by a 10-fold factor, from about 250 s to about 25 s, thus allowing for a considerably faster detection cycle without the requirement of off-line calibration steps, while not affecting the quantitative and sensitive accurate assessment of the antigen biomarkers. These results demonstrate that the simultaneous combination of bioreceptors of suitable $k_{off}$ values, along with the use of microfluidic chambers of adequate dimensions (that allow the fastest possible fluid exchange), allows for the direct fast, sensitive, and accurate detection of biomolecules based on their dissociation regimes.

The faster flow condition allows using antibody receptors, or other bioreceptors, of considerably lower affinity. The technique described in this Example can be applied to untreated blood samples. The measurements performed in this example demonstrate that a complete removal of the low-affinity nonspecific species (blood cells, proteins, salts, and small chemicals) can be achieved after a period of about 300 s, under low flow conditions, and lasting shorter, about 80 s under high flow conditions. FIG. 21 shows antigen-free untreated Blood dissociation curve under slow-flow conditions, together with a fit. The obtained $k_{off}$ was $1.6 \times 10^{-2}$ s$^{-1}$.

The present example demonstrates the application of antigen-dissociation regime from antibody-modified nanowire sensors for use in direct sensing in complex biosamples, serum and untreated blood. The technique of the present embodiments does not require ex situ time-consuming biosample manipulation steps, such as filtering, preconcentration, and desalting.

The combination of high-affinity antibody receptors, along with high solution-exchange flow rates, leads to the effective deconvolution of the complex dissociation regime window into two fully separated dissociation sub-regimes, thus allowing quantitative detection of biomarkers. The lack of ex situ biosample manipulation processes enhances the portability of the sensing platform and reduces the required volume of tested sample as it allows the direct detection of untreated biosamples (for example, from about 5 to about 10 µl µL blood or serum), reducing the detection cycle duration to less than 5 min.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method of detecting a presence and/or concentration of a marker in a liquid, the method comprising:
    contacting the liquid with a sensor having an immobilized affinity moiety interacting with the marker and being configured to generate a detectable signal responsively to said interaction, said interaction being characterized by a $K_D$ which is equal or less than $10^{-5}$ M;
    washing said liquid off said sensor; and detecting the presence and/or concentration of the marker based on a detectable signal received from said sensor within a time-window beginning after a beginning time of said washing, said detectable signal being indicative of desorption kinetic of the marker, wherein said detecting is based on said desorption kinetic.

2. The method of claim 1, wherein said marker is a biomarker.

3. The method according to claim 1, wherein said liquid is a biological liquid.

4. The method according to claim 1, comprising monitoring said detectable signal also before said beginning time of the time-window, but said detecting the presence and/or concentration of the marker is not based on any signal received from the sensor before said beginning time of the time-window.

5. The method according to claim 1, wherein said time-window begins at least 30 seconds after said beginning time of said washing.

6. The method according to claim 1, further comprising monitoring said detectable signal from said beginning time of said washing, and identifying said beginning of said time-window based on a change in a time-dependence of said signal.

7. The method according to claim 6, wherein said beginning of said time-window is defined at a time point, which is after said beginning time of said washing, and at which a rate of change of said signal, in absolute value, is below a predetermined threshold.

8. The method according to claim 1, wherein said affinity moiety comprises an immunogenic moiety.

9. The method according to claim 1, wherein said affinity moiety comprises an immunogenic moiety, which comprises an antibody or a fragment thereof.

10. The method according to claim 1, wherein said affinity moiety comprises an immunogenic moiety, which comprises an antigen, and wherein said marker is a biomarker which comprises an antibody to said antigen.

11. The method according to claim 1, wherein said affinity moiety comprises a ligand and said marker is a biomarker which comprises a receptor.

12. The method according to claim 1, wherein said sensor is a nanostructure and the affinity moiety is immobilized on a surface of said nanostructure, wherein said contacting the liquid comprises introducing the liquid to a sensing chamber containing therein said sensor and an additional sensor which is also a nanostructure but is devoid of the affinity moiety, wherein said washing comprises washing said sensing chamber, wherein the method comprises comparing a rate of returning to a baseline of said detectable signal with a rate of returning to a baseline of a background signal received from said additional sensor, and wherein said detection of the presence and/or concentration of the marker is based on said comparison.

13. The method according to claim 1, wherein said sensor is a nanostructure and the affinity moiety is immobilized on a surface of said nanostructure.

14. The method according to claim 1, wherein said sensor is a transistor.

15. The method according to claim 1, wherein said sensor is a transistor, having a nanostructure as a channel and wherein the affinity moiety is immobilized on a surface of said nanostructure.

16. The method according to claim 14, wherein said transistor is a field-effect transistor.

* * * * *